US012390167B2

(12) United States Patent
Badie et al.

(10) Patent No.: US 12,390,167 B2
(45) Date of Patent: Aug. 19, 2025

(54) METHODS AND SYSTEMS FOR DETERMINING WHETHER R-WAVE DETECTIONS SHOULD BE CLASSIFIED AS FALSE DUE TO T-WAVE OVERSENSING (TWO) OR P-WAVE OVERSENSING (PWO)

(71) Applicant: Pacesetter, Inc., Sylmar, CA (US)

(72) Inventors: Nima Badie, Oakland, CA (US); Wenwen Li, Studio City, CA (US); Fujian Qu, San Jose, CA (US); Jong Gill, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 652 days.

(21) Appl. No.: 17/723,207

(22) Filed: Apr. 18, 2022

(65) Prior Publication Data

US 2022/0401036 A1 Dec. 22, 2022

Related U.S. Application Data

(60) Provisional application No. 63/213,660, filed on Jun. 22, 2021.

(51) Int. Cl.
*A61B 5/00* (2006.01)
*A61B 5/349* (2021.01)
(Continued)

(52) U.S. Cl.
CPC ............ *A61B 5/7221* (2013.01); *A61B 5/349* (2021.01); *A61B 5/352* (2021.01); *A61B 5/353* (2021.01); *A61B 5/355* (2021.01); *A61B 5/686* (2013.01)

(58) Field of Classification Search
CPC ........... A61B 5/02–5/0295; A61B 5/30–5/308; A61B 5/318–5/367; A61B 5/686; A61B 5/7221; A61N 1/39–1/3993
See application file for complete search history.

(56) References Cited

U.S. PATENT DOCUMENTS 5,755,739 A    5/1998 Sun et al.
6,671,548 B1   12/2003 Mouchawar et al.
(Continued)

FOREIGN PATENT DOCUMENTS

CN    110680302 A    1/2020
EP      1615693 B1    1/2011
(Continued)

OTHER PUBLICATIONS

Non-final Office Action dated Sep. 11, 2024, U.S. Appl. No. 17/745,260, filed May 16, 2022.
(Continued)

*Primary Examiner* — Alyssa M Alter
(74) *Attorney, Agent, or Firm* — Pearl Cohen Zedek Latzer Baratz LLP

(57) ABSTRACT

Described herein are methods, devices and systems for determining whether an R-wave detection should be classified as a false R-wave detection due to T-wave oversensing (TWO) or P-wave oversensing (PWO). One such method includes comparing a specific morphological characteristic (e.g., peak amplitude) associated with the R-wave detection to the specific morphological characteristic associated with each R-wave detection in a first set of earlier detected R-wave detections to thereby determine whether first TWO or PWO morphological criteria are met, and in a second set of earlier detected R-wave detections to thereby determine whether second TWO or PWO morphological criteria are met, wherein the second set differs from the first set but may have some overlap with the first set.

19 Claims, 10 Drawing Sheets

(51) Int. Cl.
*A61B 5/352* (2021.01)
*A61B 5/353* (2021.01)
*A61B 5/355* (2021.01)

(56) References Cited

U.S. PATENT DOCUMENTS

| | | | |
|---|---|---|---|
| 7,027,858 B2 | 4/2006 | Cao et al. | |
| 7,155,282 B1 | 12/2006 | Min et al. | |
| 7,167,747 B2 | 1/2007 | Gunderson et al. | |
| 7,218,966 B2 | 5/2007 | Haefner | |
| 7,266,409 B2 | 9/2007 | Gunderson | |
| 7,283,863 B2 | 10/2007 | Gunderson et al. | |
| 7,333,855 B2 | 2/2008 | Gunderson et al. | |
| 7,412,282 B2 | 8/2008 | Houben | |
| 7,537,569 B2 | 5/2009 | Sarkar et al. | |
| 7,567,835 B2 | 7/2009 | Gunderson et al. | |
| 7,582,061 B2 | 9/2009 | Li et al. | |
| 7,623,911 B2 | 11/2009 | Sarkar et al. | |
| 7,630,756 B2 | 12/2009 | Linker | |
| 7,634,310 B2 | 12/2009 | Lee et al. | |
| 7,774,049 B2 | 8/2010 | Ghanem et al. | |
| 7,774,062 B2 | 8/2010 | Kim et al. | |
| 7,783,354 B2 | 8/2010 | Gunderson | |
| 7,818,056 B2 | 10/2010 | Kim et al. | |
| 7,831,301 B2 | 11/2010 | Cao et al. | |
| 7,894,893 B2 | 2/2011 | Kim et al. | |
| 7,912,545 B2 | 3/2011 | Li et al. | |
| 8,078,277 B2 | 12/2011 | Gunderson et al. | |
| 8,160,686 B2 | 4/2012 | Allavatam et al. | |
| 8,260,404 B1 | 9/2012 | Bharmi et al. | |
| 8,265,737 B2 | 9/2012 | Warren et al. | |
| 8,265,756 B1 | 9/2012 | Snell | |
| 8,406,872 B2 | 3/2013 | Stadler et al. | |
| 8,437,840 B2 | 5/2013 | Patel et al. | |
| 8,437,851 B2 | 5/2013 | Corbucci et al. | |
| 8,473,042 B2 | 6/2013 | McCarthy et al. | |
| 8,506,500 B2 | 8/2013 | Li et al. | |
| 8,521,281 B2 | 8/2013 | Patel et al. | |
| 8,538,524 B2 | 9/2013 | Rosenberg et al. | |
| 8,560,058 B2 | 10/2013 | Babaeizadeh et al. | |
| 8,560,069 B2 | 10/2013 | Zhang | |
| 8,577,455 B2 | 11/2013 | Mitrani et al. | |
| 8,583,221 B1 | 11/2013 | Patel et al. | |
| 8,588,895 B2 | 11/2013 | Sanghera et al. | |
| 8,588,896 B2 | 11/2013 | Allavatam et al. | |
| 8,600,490 B1 | 12/2013 | Bharmi | |
| 8,626,280 B2 | 1/2014 | Allavatam et al. | |
| 8,639,316 B2 | 1/2014 | Sarkar | |
| 8,744,559 B2 | 6/2014 | Houben et al. | |
| 8,750,994 B2 | 6/2014 | Ghosh et al. | |
| 8,774,909 B2 | 7/2014 | Patel et al. | |
| 8,781,585 B2 | 7/2014 | Gunderson et al. | |
| 8,792,971 B2 | 7/2014 | Gunderson et al. | |
| 8,886,296 B2 | 11/2014 | Patel | |
| 8,897,863 B2 | 11/2014 | Linker | |
| 8,914,106 B2 | 12/2014 | Charlton et al. | |
| 8,942,793 B2 | 1/2015 | Eberle et al. | |
| 8,942,795 B2 * | 1/2015 | Gunderson | A61N 1/3621 600/521 |
| 9,101,278 B2 | 8/2015 | Fischell et al. | |
| 9,167,747 B1 | 10/2015 | Andros et al. | |
| 9,307,920 B2 | 4/2016 | Mahajan et al. | |
| 9,314,210 B2 | 4/2016 | Li | |
| 9,339,662 B2 | 5/2016 | Allavatam et al. | |
| 9,381,370 B2 | 7/2016 | Gunderson | |
| 9,468,766 B2 | 10/2016 | Sheldon et al. | |
| 9,597,525 B2 * | 3/2017 | Cao | A61B 5/7264 |
| 9,675,261 B2 | 6/2017 | Cao et al. | |
| 9,682,238 B2 | 6/2017 | Zhang et al. | |
| 9,724,007 B2 | 8/2017 | Cole | |
| 9,962,100 B2 | 5/2018 | Allavatam et al. | |
| 9,993,653 B2 | 6/2018 | Bardy et al. | |
| 9,999,368 B2 | 6/2018 | Perschbacher et al. | |
| 10,004,418 B2 | 6/2018 | Cao et al. | |
| 10,183,171 B2 | 1/2019 | Ostroff et al. | |
| 10,328,274 B2 * | 6/2019 | Zhang | A61B 5/00 |
| 10,548,499 B2 | 2/2020 | Bayasi et al. | |
| 10,576,288 B2 | 3/2020 | Cao et al. | |
| 10,582,870 B2 | 3/2020 | Allavatam et al. | |
| 10,702,180 B2 | 7/2020 | Perschbacher et al. | |
| 10,709,379 B2 | 7/2020 | Warren et al. | |
| 2003/0204215 A1 | 10/2003 | Gunderson et al. | |
| 2004/0228217 A1 | 11/2004 | Szeto | |
| 2006/0224075 A1 | 10/2006 | Gunderson et al. | |
| 2007/0232948 A1 | 10/2007 | Stadler et al. | |
| 2008/0161870 A1 | 7/2008 | Gunderson | |
| 2010/0280567 A1 | 11/2010 | Gunderson | |
| 2015/0045682 A1 | 2/2015 | Sanghera et al. | |
| 2017/0354827 A1 | 12/2017 | Zhang et al. | |
| 2018/0264258 A1 | 9/2018 | Cheng et al. | |
| 2018/0311504 A1 | 11/2018 | Cao et al. | |
| 2018/0318588 A1 | 11/2018 | Dennis | |
| 2019/0329038 A1 | 10/2019 | Rhude | |
| 2020/0100694 A1 | 4/2020 | Sarkar et al. | |
| 2021/0038905 A1 | 2/2021 | Cao et al. | |
| 2021/0076964 A1 | 3/2021 | Mahajan et al. | |
| 2021/0170170 A1 | 6/2021 | Mischler et al. | |
| 2021/0236041 A1 | 8/2021 | Badie et al. | |
| 2021/0369175 A1 | 12/2021 | Badie et al. | |

FOREIGN PATENT DOCUMENTS

| | | |
|---|---|---|
| EP | 2079520 B1 | 11/2013 |
| EP | 1877137 B1 | 10/2014 |
| EP | 2967402 B1 | 1/2016 |
| EP | 2364107 B1 | 9/2016 |
| EP | 1219237 B1 | 2/2017 |
| EP | 3247453 B1 | 11/2017 |
| EP | 2895063 B1 | 1/2019 |
| EP | 3422934 B1 | 1/2019 |
| EP | 3432774 B1 | 1/2019 |
| EP | 3566746 A1 | 5/2019 |
| EP | 3592419 B1 | 1/2020 |
| EP | 2741662 B1 | 3/2021 |
| KR | 20190019668 A | 2/2019 |
| WO | WO2003/092810 A2 | 11/2003 |
| WO | WO2019/075529 A1 | 4/2019 |

OTHER PUBLICATIONS

Non-final Office Action dated Mar. 13, 2024, U.S. Appl. No. 18/146,870, filed Dec. 27, 2022.
Notice of Allowance dated Aug. 21, 2023, U.S. Appl. No. 17/223,885, filed Apr. 6, 2021.
U.S. Appl. No. 18/745,627, filed Jun. 17, 2024.
Notice of Allowance dated Dec. 21, 2022, U.S. Appl. No. 17/153,036, filed Jan. 20, 2021.
U.S. Appl. No. 18/146,870, filed Dec. 27, 2022.
"Spontaneous T-wave oversensing," Cardiocases, Pacing & Defibrillation, [https://www.cardiocases.com/en/pacingdefibrillation/clinical-situation/icd/spontaneous-t-wave-oversensing], downloaded Jun. 1, 2021, 9 pages.
U.S. Appl. No. 17/XX, filed Apr. X, 2022.
Notice of Allowance dated May 21, 2024, U.S. Appl. No. 18/146,870, filed Dec. 27, 2022.
Response to Extended European Search Report dated Apr. 13, 2023, European Patent Application No. 22169210.6.
Response to Office Action dated Oct. 25, 2024, U.S. Appl. No. 17/745,260, filed May 16, 2022.
Non-final Office Action dated Jul. 25, 2023, U.S. Appl. No. 17/223,885, filed Apr. 6, 2021.
Response to Office Action dated Jul. 31, 2023, U.S. Appl. No. 17/223,885, filed Apr. 6, 2021.
Office Action dated Dec. 6, 2023, Chinese Patent Application No. 202110598847.4.
English Abstract of CN Publication No. 110680302 published Jan. 14, 2020.
English Abstract of KR Publication No. 20190019668 published Feb. 27, 2019.

(56) References Cited

OTHER PUBLICATIONS

Response to Office Action dated Apr. 15, 2024, U.S. Appl. No. 18/146,870, filed Dec. 27, 2022.
Response to Office Action dated Apr. 15, 2024, Chinese Patent Application No. 202110598847.4.
English translation of Claims as amended in Response to Office Action dated Apr. 15, 2024, Chinese Patent Application No. 202110598847.4.
Extended European Search Report dated Sep. 9, 2022, European Patent Application No. 22169210.6.
U.S. Appl. No. 17/745,260, filed May 16, 2022.
Communication under Rule 71(3) EPC dated Oct. 8, 2024, European Patent Application No. 21170198.2-1113.
Notice of Allowance dated Feb. 20, 2025, U.S. Appl. No. 17/745,260, filed May 16, 2022.
Extended European Search Report dated Apr. 8, 2025, European Patent Application No. 25152754.5-1113.
Office Action dated Apr. 8, 2025, European Patent Application No. 21705369.3-1113.
Response to Office Action dated Jan. 2, 2025, European Patent Application No. 21705369.3-1113.
Communication under Rule 71(3) EPC dated Dec. 4, 2024, European Application No. 22169210.6-1113.
Response to Extended European Search Report dated May 15, 2025, European Patent Application No. 25152754.5-1113.
Hadjileontiadis, Leontios J., et al., "Performance Of Three QRS Detection Algorithms During Sleep: A Comparative Study," 2001 Proceedings of the 23rd Annual EMBS International Conference, Oct. 25-28, 2001, 4 pages.
Pandit, Diptangshu, et al., "A lightweight QRS detector for single lead ECG signals using a max-min difference algorithm," Computer Methods and Programs in Biomedicine, 144, Feb. 2017 15 pages.
Extended European Search Report dated Oct. 19, 2021, European Patent Application No. 21170198.2-1132.
Response to Extended European Search Report dated Feb. 4, 2022, European Patent Application No. 21170198.2-1132.
International Search Report & The Written Opinion of the International Searching Authority dated Mar. 31, 2021, International Application No. PCT/US2021/014332.

* cited by examiner

METHODS AND SYSTEMS FOR DETERMINING WHETHER R-WAVE DETECTIONS SHOULD BE CLASSIFIED AS FALSE DUE TO T-WAVE OVERSENSING (TWO) OR P-WAVE OVERSENSING (PWO)

PRIORITY CLAIM

This application claims priority to U.S. Provisional Patent Application No. 63/213,660, filed Jun. 22, 2021, titled METHODS AND SYSTEMS FOR DETERMINING WHETHER R-WAVE DETECTIONS SHOULD BE CLASSIFIED AS FALSE DUE TO T-WAVE OVERSENSING (TWO) OR P-WAVE OVERSENSING (PWO), which is incorporated herein by reference.

RELATED APPLICATION

The present application is related to U.S. patent application Ser. No. 17/153,036, titled METHODS AND SYSTEMS FOR DISTINGUISHING OVER-SENSED R-R INTERVALS FROM TRUE R-R INTERVALS, filed Jan. 20, 2021, and issued as U.S. Pat. No. 11,559,242 on Jan. 24, 2023, which is incorporated herein by reference.

FIELD OF TECHNOLOGY

Embodiments described herein relate to analysis of an electrogram (EGM) or electrocardiogram (ECG) signal, and more specifically, to determining whether an R-wave detection should be classified as false due to T-wave oversensing (TWO) or P-wave oversensing (PWO).

BACKGROUND

Various types of implantable medical devices (IMDs) are used to monitor for cardiac arrythmias. Some types of IMDs, such as implantable cardiac pacemakers and implantable cardiac defibrillators (ICDs), are capable of providing appropriate therapy in response to detected cardiac arrythmias.

The recent development of Non-vascular ICDs (NV-ICDs), otherwise known as Subcutaneous ICDs (S-ICDs), has streamlined the implantation process for ICD patients. While traditional ICDs can detect rhythms using bipolar intracardiac electrogram signals, S-ICDs rely on far-field subcutaneous EGMs. These far-field EGM, which resemble surface ECGs, often include significantly large P-waves and T-waves that can be erroneously over-sensed as an R-wave. Such oversensing can ultimately result in false detections of ventricular tachycardia (VT) or ventricular fibrillation (VF), and/or other types of arrhythmia, potentially leading to inappropriate therapy delivery (e.g., shocks). VT and VF can be detected by measuring and comparing R-R intervals, or running averages thereof, to VT and VF detection thresholds. False positive VT and VF detections are highly undesirable, because they can lead to delivery of inappropriate therapy, such as shocks, which can premature deplete the battery of an ICD, and may be painful to the patient.

Other types of IMDs, such as insertable cardiac monitors (ICMs), are used for diagnostic purposes. ICMs have been increasingly used to diagnose cardiac arrhythmias including atrial fibrillation (AF). AF is a very common type of supraventricular tachycardia (SVT) which leads to approximately one fifth of all strokes, and is the leading risk factor for ischemic stroke. However, AF is often asymptomatic and intermittent, which typically results in appropriate diagnosis and/or treatment not occurring in a timely manner. To overcome this, many cardiac devices, such as ICMs, now monitor for AF by obtaining an electrogram (EGM) signal and measuring R-R interval variability based on the EGM signal. For example, an ICM or other IMD can compare measures of R-R interval variability to a variability threshold, to automatically detect AF when the variability threshold is exceeded. Indeed, ICMs predominantly identify AF by quantifying the variability in R-R intervals (i.e., by quantifying the variability in the timing of ventricular contractions). False positive AF detections are highly undesirable, as the burden of sorting through large numbers of clinically irrelevant episodes of AF can be time consuming and costly.

Presently available P-wave and T-wave detection discriminator techniques are often unable or inadequate to correctly distinguish P-waves and T-waves from R-waves, often leading to over-sensed P-waves and over-sensed T-waves, both of which are types of false R-wave detections. Accordingly, there is a still a need for improved techniques for distinguishing P-waves and T-waves from R-waves, and for distinguishing over-sensed R-R intervals from true R-R intervals. That is, there is still a need for improved methods, devices and systems for distinguishing true R-wave detections from false R-wave detections, and more generally, for detecting T-wave oversensing (TWO) and/or P-wave oversensing (PWO).

SUMMARY

Certain embodiments of the present technology relate to methods and devices that can be used to determine whether an R-wave detection should be classified as a false R-wave detection due to TWO or PWO. In accordance with certain embodiments, a method includes comparing a specific morphological characteristic (e.g., a peak amplitude (A)) associated with an R-wave detection to the specific morphological characteristic associated with each R-wave detection in a first set of earlier detected R-wave detections to thereby determine whether first TWO or PWO morphological criteria are met, and in a second set of earlier detected R-wave detections to thereby determine whether second TWO or PWO morphological criteria are met, wherein the second set differs from the first set but may have some overlap with the first set. The method also includes determining whether to classify the R-wave detection as a false R-wave detection, based on whether one of the first or second TWO or PWO morphological criteria are met. In certain embodiments, the first set of earlier detected R-wave detections includes R-wave detections that were one, two, and three R-wave detections earlier; and the second set of earlier detected R-wave detections includes R-wave detections that were two, three, and four R-wave detections earlier. In certain such embodiments, determining whether to classify the R-wave detection as a false R-wave detection, comprises classifying the R-wave detection as a false R-wave detection in response to one of the first or the second TWO or PWO morphological criteria being met.

In accordance with certain embodiments, the specific morphological characteristic comprises a peak amplitude (A). In certain such embodiments, the first TWO or PWO morphological criteria are met when the peak amplitude $A(n)$ associated with the R-wave detection is at least a specified extent lower than a peak amplitude $A(n-1)$ associated with an R-wave detection that was one R-wave detection earlier, is not at least the specified extent lower than the peak amplitude $A(n-2)$ associated with the R-wave detection that was two R-wave detections earlier, and is at least the specified extent lower than a peak amplitude A(n−3) associated with an R-wave detection that was three R-wave detections earlier. In certain such embodiments, the second TWO or PWO morphological criteria are met when the peak amplitude A(n) associated with the R-wave detection is at least the specified extent lower than the peak amplitude A(n−2) associated with an R-wave detection that was two R-wave detections earlier, is not at least the specified extent lower than the peak amplitude A(n−3) associated with the R-wave detection that was three R-wave detections earlier, and is at least the specified extent lower than a peak amplitude A(n−4) associated with an R-wave detection that was four R-wave detections earlier.

In accordance with certain embodiments, the specific morphological characteristic comprises an area under the curve (AUC). In certain such embodiments, the first TWO or PWO morphological criteria are met when the AUC(n) associated with the R-wave detection is at least a specified extent less than an AUC(n−1) associated with an R-wave detection that was one R-wave detection earlier, is not at least the specified extent less than the AUC(n−2) associated with the R-wave detection that was two R-wave detections earlier, and is at least the specified extent less than an AUC(n−3) associated with an R-wave detection that was three R-wave detections earlier. In certain such embodiments, the second TWO or PWO morphological criteria are met when the AUC(n) associated with the R-wave detection is at least the specified extent less than the AUC(n−2) associated with an R-wave detection that was two R-wave detections earlier, is not at least the specified extent less than the AUC(n−3) associated with the R-wave detection that was three R-wave detections earlier, and is at least the specified extent less than an AUC(n−4) associated with an R-wave detection that was four R-wave detections earlier.

In accordance with certain embodiments, the specific morphological characteristic comprises a width (W) associated with the R-wave detection. In certain such embodiments, the first TWO or PWO morphological criteria are met when the width W(n) associated with the R-wave detection is at least a specified extent longer than a width W(n−1) associated with an R-wave detection that was one R-wave detection earlier, is not at least the specified extent longer than the width W(n−2) associated with the R-wave detection that was two R-wave detections earlier, and is at least the specified extent longer than a width W(n−3) associated with an R-wave detection that was three R-wave detections earlier. In certain such embodiments, the second TWO or PWO morphological criteria are met when the width W(n) associated with the R-wave detection is at least the specified extent longer than the width (n−2) associated with an R-wave detection that was two R-wave detections earlier, is not at least the specified extent longer than the width W(n−3) associated with the R-wave detection that was three R-wave detections earlier, and is at least the specified extent longer than a width W(n−4) associated with an R-wave detection that was four R-wave detections earlier. Each width can be, e.g., a measure of a full width at threshold detection crossings, a full width at half maximum (FWHM), or a half width at half maximum (HWHM) associated with respective R-wave detections.

In accordance with certain embodiments, the specific morphological characteristic comprises a maximum slope (MS) associated with the R-wave detection. In certain such embodiments, the first TWO or PWO morphological criteria are met when the MS(n) associated with the R-wave detection is at least a specified extent less than an MS(n−1) associated with an R-wave detection that was one R-wave detection earlier, is not at least the specified extent less than the MS(n−2) associated with the R-wave detection that was two R-wave detections earlier, and is at least the specified extent less than an MS(n−3) associated with an R-wave detection that was three R-wave detections earlier. In certain such embodiments, the second TWO or PWO morphological criteria are met when the MS(n) associated with the R-wave detection is at least the specified extent less than the MS(n−2) associated with an R-wave detection that was two R-wave detections earlier, is not at least the specified extent less than the MS(n−3) associated with the R-wave detection that was three R-wave detections earlier, and is at least the specified extent less than an MS(n−4) associated with an R-wave detection that was four R-wave detections earlier.

In accordance with certain embodiments, determining whether to classify the R-wave detection as a false R-wave detection, comprises classifying the R-wave detection as a false R-wave detection in response to one of the first or the second TWO or PWO morphological criteria being met.

In accordance with certain embodiments, the method further comprises comparing an R-R interval duration associated with the R-wave detection to an R-R interval duration associated with each R-wave detection in a third set of earlier detected R-wave detections to thereby determine whether first TWO or PWO temporal criteria are met, and in a fourth set of earlier detected R-wave detections to thereby determine whether second TWO or PWO temporal criteria are met, wherein the fourth set differs from the third set but may have some overlap with the third set. In such a method, determining whether to classify the R-wave detection as a false R-wave detection, is also based on whether one of the first or the second temporal criteria are met. In certain such embodiments, the third set of earlier detected R-wave detections includes R-wave detections that were one and two R-wave detections earlier; and the second set of earlier detected R-wave detections includes R-wave detections that were two and three R-wave detections earlier. In certain such embodiments, the first temporal criteria are met when the R-R interval duration D(n) associated with the R-wave detection is dissimilar to the R-R interval duration D(n−1) associated with the R-wave detection that was one R-wave detection earlier, and is similar to the R-R interval duration D(n−2) associated with the R-wave detection that was two R-wave detections earlier. The second temporal criteria are met when the R-R interval duration D(n) associated with the R-wave detection is dissimilar to the R-R interval duration D(n−2) associated with the R-wave detection that was two R-wave detections earlier, and is similar to the R-R interval duration D(n−3) associated with the R-wave detection that was three R-wave detections earlier. In certain such embodiments, determining whether to classify the R-wave detection as a false R-wave detection, comprises classifying the R-wave detection as a false R-wave detection in response to both the first TWO or PWO morphological criteria and the first temporal criteria being met, or both the second TWO or PWO morphological criteria and the second TWO or PWO morphological criteria being met.

In accordance with certain embodiments of the present technology, a device comprises two or more electrodes, a sensing circuit, and a processor or controller. The sensing circuit is coupled to the two or more electrodes and configured to obtain one or more ECG or EGM signals indicative of electrical activity of a patient's heart. With such a device, which can be an implantable medical device (IMD), R-wave detections are made based on comparisons of the signal indicative of electrical activity of the patient's heart, or samples thereof, to an R-wave detection threshold. In accordance with certain embodiments, in order to determine whether an R-wave detection should be classified as a false R-wave detection due to TWO or PWO, the processor or controller is configured to compare a specific morphological characteristic associated with the R-wave detection to the specific morphological characteristic associated with each R-wave detection in a first set of earlier detected R-wave detections to thereby determine whether first TWO or PWO morphological criteria are met, and in a second set of earlier detected R-wave detections to thereby determine whether second TWO or PWO morphological criteria are met, wherein the second set differs from the first set but may have some overlap with the first set. Additionally, the processor or controller is configured to determine whether to classify the R-wave detection as a false R-wave detection, based on whether one of the first or second TWO or PWO morphological criteria are met.

In accordance with certain embodiments, the first set of earlier detected R-wave detections includes R-wave detections that were one, two, and three R-wave detections earlier; and the second set of earlier detected R-wave detections includes R-wave detections that were two, three, and four R-wave detections earlier. In certain such embodiments, the processor or controller is configured to classify the R-wave detection as a false R-wave detection in response to one of the first or the second TWO or PWO morphological criteria being met.

In accordance with certain embodiments, the specific morphological characteristic comprises a peak amplitude (A). In certain such embodiments, the processor or controller is configured to determine that the first TWO or PWO morphological criteria are met when the peak amplitude $A(n)$ associated with the R-wave detection is at least a specified extent lower than a peak amplitude $A(n-1)$ associated with an R-wave detection that was one R-wave detection earlier, is not at least the specified extent lower than the peak amplitude $A(n-2)$ associated with the R-wave detection that was two R-wave detections earlier, and is at least the specified extent lower than a peak amplitude $A(n-3)$ associated with an R-wave detection that was three R-wave detections earlier. The processor or controller is configured to determine that the second TWO or PWO morphological criteria are met when the peak amplitude $A(n)$ associated with the R-wave detection is at least the specified extent lower than the peak amplitude $A(n-2)$ associated with an R-wave detection that was two R-wave detections earlier, is not at least the specified extent lower than the peak amplitude $A(n-3)$ associated with the R-wave detection that was three R-wave detections earlier, and is at least the specified extent lower than a peak amplitude $A(n-4)$ associated with an R-wave detection that was four R-wave detections earlier.

In accordance with certain embodiments, the specific morphological characteristic comprises an area under the curve (AUC). In certain such embodiments, the processor or controller is configured to determine that the first TWO or PWO morphological criteria are met when the $AUC(n)$ associated with the R-wave detection is at least a specified extent less than an $AUC(n-1)$ associated with an R-wave detection that was one R-wave detection earlier, is not at least the specified extent less than the $AUC(n-2)$ associated with the R-wave detection that was two R-wave detections earlier, and is at least the specified extent less than an $AUC(n-3)$ associated with an R-wave detection that was three R-wave detections earlier. The processor or controller is configured to determine that the second TWO or PWO morphological criteria are met when the $AUC(n)$ associated with the R-wave detection is at least the specified extent less than the $AUC(n-2)$ associated with an R-wave detection that was two R-wave detections earlier, is not at least the specified extent less than the $AUC(n-3)$ associated with the R-wave detection that was three R-wave detections earlier, and is at least the specified extent less than an $AUC(n-4)$ associated with an R-wave detection that was four R-wave detections earlier.

In accordance with certain embodiments, the specific morphological characteristic comprises a width (W) associated with the R-wave detection. In certain such embodiments, the processor or controller is configured to determine that the first TWO or PWO morphological criteria are met when the width $W(n)$ associated with the R-wave detection is at least a specified extent longer than a width $W(n-1)$ associated with an R-wave detection that was one R-wave detection earlier, is not at least the specified extent longer than the width $W(n-2)$ associated with the R-wave detection that was two R-wave detections earlier, and is at least the specified extent longer than a width $W(n-3)$ associated with an R-wave detection that was three R-wave detections earlier. The processor or controller is configured to determine that the second TWO or PWO morphological criteria are met when the width $W(n)$ associated with the R-wave detection is at least the specified extent longer than the width $(n-2)$ associated with an R-wave detection that was two R-wave detections earlier, is not at least the specified extent longer than the width $W(n-3)$ associated with the R-wave detection that was three R-wave detections earlier, and is at least the specified extent longer than a width $W(n-4)$ associated with an R-wave detection that was four R-wave detections earlier. Each width can be, e.g., a measure of a full width at threshold detection crossings, a FWHM, or a HWHM associated with respective R-wave detections.

In accordance with certain embodiments, the specific morphological characteristic comprises a maximum slope (MS) associated with the R-wave detection. In certain such embodiments, the processor or controller is configured to determine that the first TWO or PWO morphological criteria are met when the $MS(n)$ associated with the R-wave detection is at least a specified extent less than an $MS(n-1)$ associated with an R-wave detection that was one R-wave detection earlier, is not at least the specified extent less than an $MS(n-2)$ associated with the R-wave detection that was two R-wave detections earlier, and is at least the specified extent less than an $MS(n-3)$ associated with an R-wave detection that was three R-wave detections earlier. The processor or controller is configured to determine that the second TWO or PWO morphological criteria are met when the $MS(n)$ associated with the R-wave detection is at least the specified extent less than the $MS(n-2)$ associated with the R-wave detection that was two R-wave detections earlier, is not at least the specified extent less than the $MS(n-3)$ associated with the R-wave detection that was three R-wave detections earlier, and is at least the specified extent less than an $MS(n-4)$ associated with an R-wave detection that was four R-wave detections earlier.

In accordance with certain embodiments, the controller or processor is configured to classify the R-wave detection as a false R-wave detection in response to one of the first or the second TWO or PWO morphological criteria being met.

In accordance with certain embodiments, the controller or processor is also configured to compare an R-R interval duration associated with the R-wave detection to an R-R interval duration associated with each R-wave detection in a third set of earlier detected R-wave detections to thereby determine whether first TWO or PWO temporal criteria are met, and in a fourth set of earlier detected R-wave detections to thereby determine whether second TWO or PWO temporal criteria are met, wherein the fourth set differs from the third set but may have some overlap with the third set. In certain such embodiments, the processor or controller is configured to determine whether to classify the R-wave detection as a false R-wave detection, also based on whether one of the first or the second temporal criteria are met.

In accordance with certain embodiments, the third set of earlier detected R-wave detections includes R-wave detections that were one and two R-wave detections earlier; and the second set of earlier detected R-wave detections includes R-wave detections that were two and three R-wave detections earlier. In certain such embodiments, the processor or controller is configured to determine that the first temporal criteria are met when the R-R interval duration D(n) associated with the R-wave detection is dissimilar to an R-R interval duration D(n-1) associated with the R-wave detection that was one R-wave detection earlier, and is similar to an R-R interval duration D(n-2) associated with the R-wave detection that was two R-wave detections earlier. The processor or controller is configured to determine that the second temporal criteria are met when the R-R interval duration D(n) associated with the R-wave detection is dissimilar to the R-R interval duration D(n-2) associated with the R-wave detection that was two R-wave detections earlier, and is similar to an R-R interval duration D(n-3) associated with an R-wave detection that was three R-wave detections earlier.

In accordance with certain embodiments, the controller or processor is configured to classify the R-wave detection as a false R-wave detection in response to both the first TWO or PWO morphological criteria and the first temporal criteria being met, or both the second TWO or PWO morphological criteria and the second TWO or PWO morphological criteria being met.

In accordance with certain embodiments, the controller or processor is further configured to adjust at least one parameter of the R-wave detection threshold based on results of determinations of whether R-wave detections should be classified as false R-wave detections due to TWO or PWO. For example, if at least a threshold number of R-wave detections within a specified number of R-wave detections (or within a specified amount of time) are classified as being false R-wave detections due to PWO, then an R-wave detection threshold can be increased to reduce the chance of PWO. Alternatively, or additionally, if at least a threshold number of R-wave detections within a specified number of R-wave detections (or within a specified amount of time) are classified as being false R-wave detections due to TWO, then a delay decay of an R-wave detection threshold can be prolonged to reduce the chance of TWO, wherein the decay delay defines the interval at which a magnitude or sensitivity level of an R-wave detection threshold remains at a constant level following expiration of a refractory period before the R-wave detection threshold begins decreasing in real time.

Certain embodiments of the present technology are directed to a method for determining whether an R-wave detection should be classified as a false R-wave detection due to TWO or P-wave oversensing PWO, the method comprising: obtaining a peak amplitude A(n) associated with an R-wave detection and a respective peak amplitude for other R-wave detections preceding the R-wave detection; determining whether first TWO or PWO morphological criteria are met by determining whether the peak amplitude A(n) associated with the R-wave detection is at least a specified extent lower than a peak amplitude A(n-1) associated with an R-wave detection that was one R-wave detection earlier, is not at least the specified extent lower than the peak amplitude A(n-2) associated with the R-wave detection that was two R-wave detections earlier, and is at least the specified extent lower than a peak amplitude A(n-3) associated with an R-wave detection that was three R-wave detections earlier; determining whether second TWO or PWO morphological criteria are met by determining whether the peak amplitude A(n) associated with the R-wave detection is at least the specified extent lower than the peak amplitude A(n-2) associated with an R-wave detection that was two R-wave detections earlier, is not at least the specified extent lower than the peak amplitude A(n-3) associated with the R-wave detection that was three R-wave detections earlier, and is at least the specified extent lower than a peak amplitude A(n-4) associated with an R-wave detection that was four R-wave detections earlier; and classifying the R-wave detection as a false R-wave detection in response to one of the first or the second TWO or PWO morphological criteria being met.

Certain embodiments of the present technology are directed to a device comprising: two or more electrodes; a sensing circuit coupled to the two or more electrodes and configured to obtain a signal indicative of electrical activity of a patient's heart; and a processor or controller. The processor or controller is configured to obtain a peak amplitude A(n) associated with an R-wave detection and a respective peak amplitude for other R-wave detections preceding the R-wave detection. The processor or controller is also configured to determine whether first TWO or PWO morphological criteria are met by determining whether the peak amplitude A(n) associated with the R-wave detection is at least a specified extent lower than a peak amplitude A(n-1) associated with an R-wave detection that was one R-wave detection earlier, is not at least the specified extent lower than a peak amplitude A(n-2) associated with an R-wave detection that was two R-wave detections earlier, and is at least the specified extent lower than a peak amplitude A(n-3) associated with an R-wave detection that was three R-wave detections earlier. The processor or controller is also configured to determine whether second TWO or PWO morphological criteria are met by determining whether the peak amplitude A(n) associated with the R-wave detection is at least the specified extent lower than the peak amplitude A(n-2) associated with the R-wave detection that was two R-wave detections earlier, is not at least the specified extent lower than the peak amplitude A(n-3) associated with the R-wave detection that was three R-wave detections earlier, and is at least the specified extent lower than a peak amplitude A(n-4) associated with an R-wave detection that was four R-wave detections earlier. The processor or controller is configured to classify the R-wave detection as a false R-wave detection in response to one of the first or the second TWO or PWO morphological criteria being met.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

DETAILED DESCRIPTION

Figure 1:
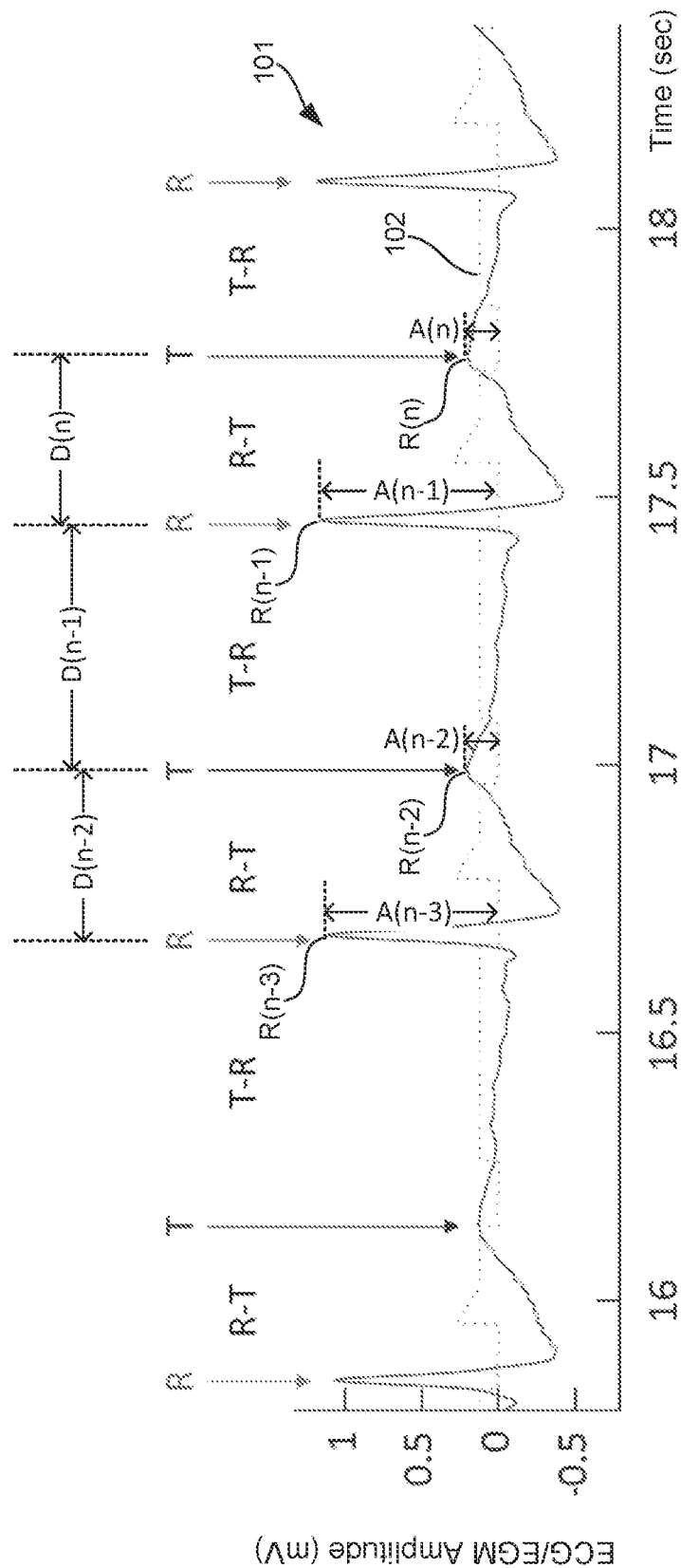
FIG. 1 illustrates an example EGM signal and is used to explain how certain criteria, often referred to first TWO or PWO temporal criteria and first TWO or PWO morphological criteria, can be used to determine whether an R-wave detection should be classified as a false R-wave detection.

It is well known that each cardiac cycle represented within an EGM or ECG typically includes a P-wave, followed by a QRS complex, followed by a T-wave, with the QRS complex including Q-, R-, and S-waves. The P-wave is caused by depolarization of the atria. This is followed by atrial contraction, which is indicated by a slight rise in atrial pressure contributing to further filling of the ventricle. Following atrial contraction is ventricular depolarization, as indicated by the QRS complex, with ventricular depolarization initiating contraction of the ventricles resulting in a rise in ventricular pressure until it exceeds the pulmonary and aortic diastolic pressures to result in forward flow as the blood is ejected from the ventricles. Ventricular repolarization occurs thereafter, as indicated by the T-wave and this is associated with the onset of ventricular relaxation in which forward flow stops, the pressure in the ventricle falls below that in the atria at which time the mitral and tricuspid valves open to begin to passively fill the ventricle during diastole. The terms EGM, EGM signal, and EGM waveform are used interchangeably herein. Similarly, the terms ECG, ECG signal, and ECG waveform are used interchangeably herein. Both ECG and EGM signals are signals indicative of electrical activity of a patient's heart, and each may also be referred to as a signal indicative of cardiac electrical activity.

The R-wave is the largest wave in the QRS complex, and it often identified by comparing samples of an EGM or ECG to an R-wave threshold, wherein the R-wave threshold is typically variable and typically depends on peak amplitudes of detected R-waves. Various measurements can be obtained based on the EGM or ECG waveform, including measurements of R-R intervals, where an R-R interval is the duration between a pair of consecutive R-waves. As noted above, in the Background, a common technique for detecting AF is based on measures of R-R interval variability, and common techniques for detecting VT and VF is based on measures of R-R interval durations or running averages thereof. However, where T-waves and/or P-waves are falsely identified as R-waves, because they are over-sensed, false R-R intervals can be identified which have a high variability, leading to false detections of AF. Overs-sensed T-waves and/or P-waves can also lead to false detections of VT and VF. In other words, over-sensed P-waves and/or over-sensed T-waves can lead to false positive AF detections, false positive VT detections, and/or false positive VF detections. An over-sensed P-wave, as the term is used herein, refers to a P-wave that is falsely identified as an R-wave. Similarly, an over-sensed T-wave, as the term is used herein, refers to a T-wave that is falsely identified as an R-wave. Accordingly, it can be appreciated that over-sensed T-waves and over-sensed P-waves are examples of false R-wave detections that are due to T-wave oversensing (TWO) and P-wave oversensing (PWO), respectively.

Certain embodiments of the present technology relate to methods and devices that use R-R interval durations and peak amplitudes (or other types of temporal and/or morphological characteristics) associated with R-wave detections to determine whether P-wave and/or T-wave oversensing has occurred, and more generally, to distinguish true R-wave detections from false R-wave detections. Such embodiments can beneficially be used, for example, to prevent or reject false positive VF detections, to prevent or reject false positive VT detections, and/or to prevent or reject false positive AF detections, but are not limited thereto. Accordingly, it would be appreciated that such embodiments can be used to provide for improved delivery of therapy and/or improved use of clinical resources. For example, where an embodiment of the present technology is used to prevent or reject a false positive detection of VF, the embodiment can be used to avoid delivery of a defibrillation shock that is unnecessary, painful to the patient, and prematurely depletes power from a battery of an IMD. For another example, where an embodiment of the present technology is used to prevent or reject a false positive detection of VT, the embodiment can be used to avoid delivery of anti-tachycardia pacing (ATP) that is unnecessary, may accelerate sinus rhythm to VT or VF, and prematurely depletes power from a battery of an IMD. For still another example, where an embodiment of the present technology is used to prevent or reject a false positive detection of AF, the embodiment can be used to improve the use of clinical resources, where clinicians are tasked with analyzing AF episodes that are detected and recorded by an IMD.

A true R-R interval, as the term is used herein, refers to an actual R-R interval, which is the interval between two actual R-waves. A false R-R interval, as the term is used herein, refers to an interval that is mistakenly identified as an R-R interval, but is not an actual R-R interval. Example types of intervals that may be mistakenly identified as an R-R interval, and thus are examples of false R-R intervals, include, but are not limited to, P-R intervals, R-T intervals, P-T intervals, and T-P intervals. A P-R interval can be mistakenly identified as an R-R interval where a P-wave is over-sensed. An R-T interval can be mistakenly identified as R-R interval where a T-wave is over-sensed. A P-T interval or a T-P interval can be mistakenly identified as an R-R interval where T- and P-waves are over-sensed and an R-wave is under-sensed. These are just a few examples of types of false R-R intervals and how they may occur, which examples are not intended to be all inclusive. False R-R intervals can also be referred to herein as over-sensed R-R intervals.

An R-R interval is the duration between two consecutive R-wave detections, and thus, an R-R interval can also be referred to herein as an R-R duration. More generally, an R-wave detection can be said to have an associated R-R interval duration, which is the duration between the time of the R-wave detection and the time of the immediately preceding R-wave detection. When discussing an R-wave detection, the immediately preceding R-wave detection can also be referred to as an R-wave detection that was one R-wave detection earlier. The duration that is associated with an R-wave detection can be determined by a processor of an IMD, as could other temporal and/or morphological characteristics that are associated with the R-wave detection. For example, a peak amplitude associated with an R-wave detection can be determined, e.g., by determining a peak amplitude of an ECG or EGM signal within a window (e.g., a refractory window, but not limited thereto) that follows the R-wave detection. Examples of other morphological characteristics that can be determined for an R-wave detection include, but are not limited to, a maximum slope of the ECG or EGM signal within a specified window surrounding or following the R-wave detection, a width associated with the R-wave detection, ECG or EGM signal morphology correlation, an area under the curve (AUC) associated with the R-wave detection, a peak amplitude polarity of the R-wave detection, and/or the like. For most of the remaining discussion, it is assumed that the morphological characteristic associated with an R-wave detection, which is used to determine whether or not the R-wave detection should be classified as a false R-wave detection, is the peak amplitude associated with the R-wave detection. Additionally, for most of the remaining discussion, it is assumed that the temporal characteristic associated with an R-wave detection, which is used to determine whether or not the R-wave detection should be classified as a false R-wave detection, is an R-R interval duration associated with the R-wave detection, wherein the associated R-R interval duration is the duration (i.e., length of time) between the R-wave detection and an R-wave detection that was one R-wave detection earlier.

Certain embodiments of the present technology described herein rely on various criteria to identify a false R-wave detection. One criteria, which can be referred to as first TWO or PWO temporal criteria, is that an R-R interval duration D(n) associated with an R-wave detection that is actually an over-sensed P-wave or T-wave should be dissimilar to an R-R interval duration associated with an R-wave detection D(n−1) that was one R-wave detection earlier, and should be similar an R-R interval duration associated with an R-wave detection D(n−2) that was two R-wave detections earlier. As will be appreciated from the discussion below, the term "dissimilar" when used herein to describe how two R-R interval durations compare, means that a difference in the durations, however calculated, is beyond some specified threshold. The term "similar" when used herein to describe how two R-R interval durations compare, means that a difference in the durations, however calculated, is within some specified threshold. If two R-R interval durations are not similar to one another, because the difference in their durations is beyond the specified threshold, then it can also be said that the two R-R interval durations are dissimilar.

Another criteria, which can be referred to as first TWO or PWO morphological criteria, is that a peak amplitude A(n) associated with an R-wave detection that is actually an over-sensed P-wave or T-wave should be lower than a peak amplitude associated with an R-wave detection that was one R-wave detection earlier A(n−1), lower than a peak amplitude A(n−3) of an R-wave detection that was three R-wave detections earlier A(n−3), but not lower than a peak amplitude of an R-wave detection that was two R-wave detections earlier A(n−2). As will be appreciated from the discussion below, the term "lower" when used herein to describe how two peak amplitudes compare, means a value of one peak amplitude is less than a value of another peak amplitude by at least some specified threshold, or that a ratio of the values of the two peak amplitudes is below some specified threshold. It is noted that the phrase "TWO or PWO", which refers to T-wave oversensing or P-wave oversensing, can alternatively be written as TWO/PWO.

In accordance with certain embodiments, if the first TWO or PWO temporal criteria and the first TWO or PWO morphological criteria are both met for an R-wave detection, then the R-wave detection is classified as being a false R-wave detection, which may be caused by either P-wave oversensing (PWO) or T-wave oversensing (TWO). The first TWO or PWO temporal criteria and the first TWO or PWO morphological criteria can both be met, e.g., where an R-wave detection actually corresponds to a T-wave, an R-wave detection that corresponds to one R-wave detection earlier is a true R-wave, an R-wave detection that corresponds to two R-wave detections earlier is a T-wave, and an R-wave detection that corresponds to three R-wave detections earlier is a true R-wave. An example of this is shown in FIG. 1, discussed below. Alternatively, the first TWO or PWO temporal criteria and the first TWO or PWO morphological criteria can both be met, e.g., where an R-wave detection actually corresponds to a P-wave, an R-wave detection that corresponds to one R-wave detection earlier is a true R-wave, an R-wave detection that corresponds to two R-wave detections earlier is a P-wave, and an R-wave detection that corresponds to three R-wave detections earlier is a true R-wave.

If the first TWO or PWO temporal criteria and the first TWO or PWO morphological criteria are not both met for an R-wave detection, then in accordance with certain embodiments of the present technology, the R-wave detection may still be classified as a false R-wave detection if both of second TWO or PWO temporal criteria and second TWO or PWO morphological criteria, which are discussed below, are met.

Figure 2:
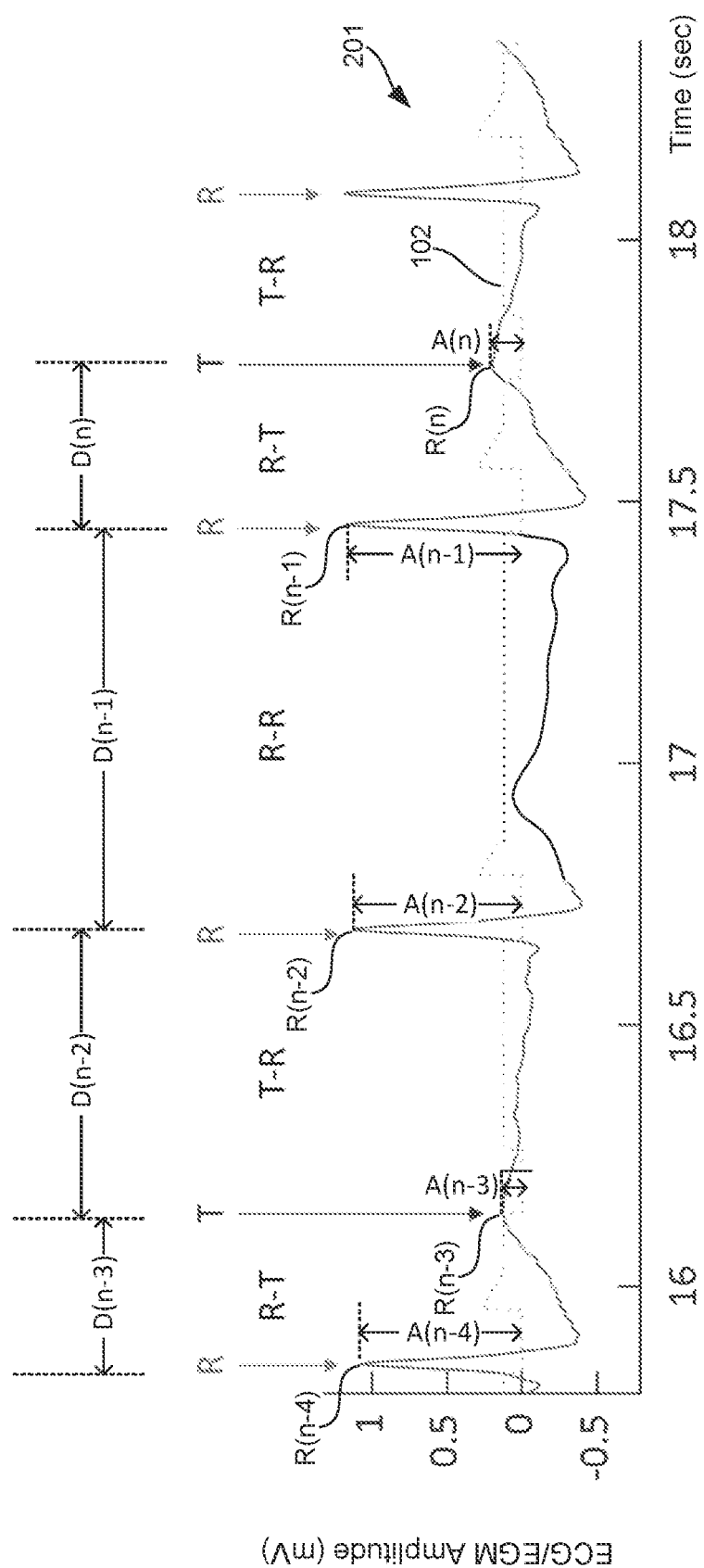
FIG. 2 illustrates an example EGM signal and is used to explain how certain other criteria, often referred to second TWO or PWO temporal criteria and second TWO or PWO morphological criteria, can be used to determine whether an R-wave detection should be classified as a false R-wave detection.

The second TWO or PWO temporal criteria, according to an embodiment, is that an R-R interval duration D(n) associated with an R-wave detection that is actually an over-sensed P-wave or T-wave should be different than (i.e., dissimilar to) an R-R interval duration associated with an R-wave detection that was two R-wave detections earlier D(n−2), and should be similar an R-R interval duration associated with an R-wave detection that was three R-wave detections earlier D(n−3). The second TWO or PWO morphological criteria, according to an embodiment, is that a peak amplitude A(n) associated with an R-wave detection that is actually an over-sensed P-wave or T-wave should be lower than a peak amplitude associated with an R-wave detection that was two R-wave detections earlier A(n−2), lower than a peak amplitude of an R-wave detection that was four R-wave detections earlier A(n−4), but not lower than a peak amplitude of an R-wave detection that was three R-wave detections earlier A(n−3). The second TWO or PWO temporal criteria and the second TWO or PWO morphological criteria can both be met, e.g., where an R-wave detection actually corresponds to a T-wave, an R-wave detection that corresponds to one R-wave detection earlier is a true R-wave, an R-wave detection that corresponds to two R-wave detections earlier is a true R-wave, an R-wave detection that corresponds to three R-wave detections earlier is a T-wave, and an R-wave detection that corresponds to four R-wave detections earlier is a true R-wave. An example of this is shown in FIG. 2, discussed below. Alternatively, the second TWO or PWO temporal criteria and the second TWO or PWO morphological criteria can both be met, e.g., where an R-wave detection actually corresponds to a P-wave, an R-wave detection that corresponds to one R-wave detection earlier is a true R-wave, an R-wave detection that corresponds to two R-wave detections earlier is a true R-wave, an R-wave detection that corresponds to three R-wave detections earlier is a P-wave, and an R-wave detection that corresponds to four R-wave detections earlier is a true R-wave.

In summary, in accordance with certain embodiments, an R-wave detection is classified as a false R-wave if either: the first TWO or PWO temporal criteria and the first TWO or PWO morphological criteria are both met; or the second TWO or PWO temporal criteria and the second TWO or PWO morphological criteria are both met. These criteria are described in additional detail below with reference to FIGS. 1 and 2.

FIG. 1 shows an example EGM signal 101 sensed by an IMD, such as an S-ICD. The R-wave detection that is being analyzed is the R-wave detection labeled R(n) in FIG. 1, which has an associated R-R interval duration D(n), and an associated peak amplitude A(n). As noted above, in accordance with an embodiment the first TWO or PWO temporal criteria is that an R-R interval duration D(n) associated with an R-wave detection that is actually an over-sensed P-wave or T-wave should be different than an R-R interval duration associated with an R-wave detection that was one R-wave detection earlier D(n−1), and should be similar an R-R interval duration associated with an R-wave detection that was two R-wave detections earlier D(n−2). In accordance with certain embodiments, in order to determine whether D(n) is different than D(n−1), a percentage difference between D(n) and D(n−1) is determined and compared to a corresponding percentage threshold, e.g., 10%. Similarly, in order to determine whether D(n) is similar to D(n−2), a percentage difference between D(n) and D(n−2) is determined and compared to the corresponding percentage threshold, e.g., 10%. The percentage difference between D(n) and D(n−1) can be calculated using the equation: % Difference D(n) vs. D(n−1)=100*|D(n)−D(n−1)|/D(n). Similarly, the percentage difference between D(n) and D(n−2) can be calculated using the equation: % Difference D(n) vs. D(n−2)=100*|D(n)−D(n−2)|/D(n). It can be appreciated from FIG. 1 that the % Difference D(n) vs. D(n−1)=100*|D(n)−D(n−1)|/D(n)=100*|0.30-0.45|/0.3=50%>10%. It can also be appreciated from FIG. 1 that % Difference D(n) vs. D(n−2)=100*|D(n)−D(n−2)|/D(n)=100*|0.30−0.29|/0.30=3.3%<10%.

As noted above, in accordance with an embodiment the first TWO or PWO morphological criteria is that a peak amplitude A(n) associated with an R-wave detection that is actually an over-sensed P-wave or T-wave should be lower than a peak amplitude A(n−1) associated with an R-wave detection that was one R-wave detection earlier, not lower than a peak amplitude A(n−2) of an R-wave detection that was two R-wave detections earlier, and lower than a peak amplitude A(n−3) of an R-wave detection that was three R-wave detections earlier. In accordance with certain embodiments, in order to determine whether A(n) is lower than A(n−1), a ratio of A(n) to A(n−1) is determined and compared to a corresponding ratio threshold, e.g., 0.4. Similarly, in order to determine whether A(n) is not lower than A(n−2), a ratio of A(n) to A(n−2) is determined and compared to the corresponding ratio threshold, e.g., 0.4. Further, in order to determine whether A(n) is lower than A(n−3), a ratio of A(n) to A(n−3) is determined and compared to the corresponding ratio threshold, e.g., 0.4. The aforementioned ratios can be calculated using the equations: Ratio A(n) vs. A(n−1)=A(n)/A(n−1); Ratio A(n) vs. A(n−2)=A(n)/A(n−2); and Ratio A(n) vs. A(n−3)=A(n)/A(n−3). It can be appreciated from FIG. 1 that Ratio A(n) vs. A(n−1)=A(n)/A(n−1)=0.2/1.2=0.17<0.4. It can also be appreciated from FIG. 1 that Ratio A(n) vs. A(n−2)=A(n)/A(n−2)=0.2/0.2=1>0.4. Further, it can be appreciated from FIG. 1 that Ratio A(n) vs. A(n−3)=A(n)/A(n−3)=0.2/1.2=0.17<0.4.

As can be appreciated from the above example, which was described with reference to FIG. 1, in this example both the first TWO or PWO temporal criteria and the first TWO or PWO morphological criteria are met, and thus, using an embodiment of the present technology the R-wave detection R(n) would be classified as a false R-wave detection that is due to TWO or PWO.

As noted above, if the first TWO or PWO temporal criteria and the first TWO or PWO morphological criteria are not both met for an R-wave detection, the R-wave detection can still be classified as a false R-wave detection if the second TWO or PWO temporal criteria and the second TWO or PWO morphological criteria are both met. That is because an R-wave detection is classified as a false R-wave if either: the first TWO or PWO temporal criteria and first TWO or PWO morphological criteria are both met; or the second TWO or PWO temporal criteria and the second TWO or PWO morphological criteria are both met.

FIG. 2 shows an example EGM signal 201 sensed by an IMD, such as an S-ICD. The R-wave detection that is being analyzed is the R-wave detection labeled R(n) in FIG. 2, which has an associated R-R interval duration D(n), and an associated peak amplitude A(n). As noted above, the second TWO or PWO temporal criteria according to an embodiment is that an R-R interval duration D(n) associated with an R-wave detection that is actually an over-sensed P-wave or T-wave should be different than an R-R interval duration associated with an R-wave detection that was two R-wave detections earlier D(n−2), and should be similar an R-R interval duration associated with an R-wave detection that was three R-wave detections earlier D(n−3). In accordance with certain embodiments, in order to determine whether D(n) is different than D(n−2), a percentage difference between D(n) and D(n−2) is determined and compared to a corresponding percentage threshold, e.g., 10%. Similarly, in order to determine whether D(n) is similar to D(n−3), a percentage difference between D(n) and D(n−3) is determined and compared to the corresponding percentage threshold, e.g., 10%. The percentage difference between D(n) and D(n−2) can be calculated using the equation: % Difference D(n) vs. D(n−2)=100*|D(n)−D(n−2)|/D(n). Similarly, the percentage difference between D(n) and D(n−3) can be calculated using the equation: % Difference D(n) vs. D(n−3)=100*|D(n)−D(n−3)|/D(n). It can be appreciated from FIG. 2 that the % Difference D(n) vs. D(n−2)=100*|D(n)−D(n−2)|/D(n)=100*|0.3−0.6|/0.3=100%>10%. It can also be appreciated from FIG. 1 that % Difference D(n) vs. D(n−3)=100*|D(n)−D(n−2)|/D(n)=100*|0.3−0.29|/0.3=3.3%<10%.

As noted above, the second TWO or PWO morphological criteria according to an embodiment is that a peak amplitude A(n) associated with an R-wave detection that is actually an over-sensed P-wave or T-wave should be lower than a peak amplitude A(n−2) associated with an R-wave detection that was two R-wave detections earlier, not lower than a peak amplitude A(n−3) of an R-wave detection that was three R-wave detections earlier, and lower than a peak amplitude A(n−4) of an R-wave detection that was four R-wave detections earlier. In accordance with certain embodiments, in order to determine whether A(n) is lower than A(n−2), a ratio of A(n) to A(n−2) is determined and compared to a corresponding ratio threshold, e.g., 0.4. Similarly, in order to determine whether A(n) is not lower than A(n−3), a ratio of A(n) to A(n−3) is determined and compared to the corresponding ratio threshold, e.g., 0.4. Further, in order to determine whether A(n) is lower than A(n−4), a ratio of A(n) to A(n−4) is determined and compared to the corresponding ratio threshold, e.g., 0.4. The aforementioned ratios can be calculated using the equations: Ratio A(n) vs. A(n−2)=A(n)/A(n−2); Ratio A(n) vs. A(n−3)=A(n)/A(n−3); and Ratio A(n) vs. A(n−4)=A(n)/A(n−4). It can be appreciated from FIG. 2 that Ratio A(n) vs. A(n−2)=A(n)/A(n−2)=0.2/1.1=0.18<0.4. It can also be appreciated from FIG. 1. that Ratio A(n) vs. A(n−3)=A(n)/A(n−3)=0.2/0.15=1.3>0.4. Further, it can be appreciated from FIG. 1 that that Ratio A(n) vs. A(n−4)=A(n)/A(n−4)=0.2/1.2=0.17<0.4.

As can be appreciated from the above example, which was described with reference to FIG. 2, in this example both the second TWO or PWO temporal criteria and the second TWO or PWO morphological criteria are met, and thus, using an embodiment of the present technology the R-wave detection R(n) would be classified as a false R-wave detection.

In alternative embodiments, when determining whether the first TWO or PWO temporal criteria or the second TWO or PWO temporal criteria are met, rather than using percentage differences to compare the R-R interval durations associated with various R-wave detections to one another, ratios can instead be used. For example, in order to determine whether D(n) is different in duration to D(n−1) there can be a determination of D(n) vs. D(n−1)=D(n)/D(n−1), which can be compared to a threshold. For example, if the ratio D(n)/D(n−1) is within the range of 0.9 to 1.1 then the durations are considered to be similar, and if that ratio D(n)/D(n−1) is outside that range then the durations are considered to be dissimilar. Still other ways of determining whether durations are similar or dissimilar to one another are also possible and are within the scope of the embodiments described herein. Other thresholds, besides the example thresholds described herein, can alternatively be used.

In alternative embodiments, when determining whether the first TWO or PWO morphological criteria or the second TWO or PWO morphological criteria are met, rather than using ratios to compare the amplitudes associated with the various R-wave detections to one another, percentage difference can instead be used. For example, in order to determine whether and to what extent A(n) is lower than A(n−2), there can be a determination of the % Difference A(n) vs. A(n−2)=100*(A(n)−A(n−2))/D(n), which can be compared to a threshold of, e.g., −60%. Still other ways of determining whether one peak amplitude is lower than another peak amplitude are possible and are within the scope of the embodiments described herein. It is also noted that one or more other types of morphological characteristics associated with R-wave detections can be compared to one another, besides (instead of, or in addition to) peak amplitudes, in order to determine whether an R-wave detection should be classified as a false R-wave detection. As noted above, examples of other morphological characteristics that can be determined for an R-wave detection (and used to determine whether an R-wave detection should be classified as a false R-wave detection), include, but are not limited to, a maximum slope (MS) within a window surrounding or following the R-wave detection, a width (W) associated with the R-wave detection, a ECG or EGM signal morphology correlation, an area under the curve (AUC) associated with the R-wave detection, a peak amplitude polarity of the R-wave detection, and/or the like. The maximum slope can be determined by determining a maximum derivative (dV/dt) of an ECG or EGM signal within a window surrounding or following the R-wave detection. Such a window can be, e.g., a window that is from 50 milliseconds (msec) prior to the R-wave detection to 50 msec following the R-wave detection. Such a morphological characteristic may be used to distinguish an over-sensed P-wave or T-wave from a true R-wave since the maximum slope of a P-wave or T-wave is typically lower than the maximum slope of a true R-wave, similar to the peak amplitude of a P-wave or T-wave typically being lower than the peak amplitude of a true R-wave. Similarly, the area under the curve of a P-wave or T-wave between zero crossings is typically less than the area under the curve of a true R-wave between zero crossings. By contrast, the width of a P-wave or T-wave is typically greater than the width a true R-wave, and thus, if such a morphological characteristic is used in comparisons, the logic used in the comparison should be modified accordingly, as would be appreciated by one of ordinary skill in the art reading this disclosure.

For the remaining discussion, unless stated otherwise, it is assumed that the morphological characteristic associated with an R-wave detection, which is used to determine whether or not the R-wave detection should be classified as a false R-wave detection, is the peak amplitude associated with the R-wave detection. Additionally, for the remaining discussion, unless stated otherwise, it is assumed that the temporal characteristic associated with an R-wave detection, which is used to determine whether or not the R-wave detection should be classified as a false R-wave detection, is an R-R interval duration associated with the R-wave detection, wherein the associated R-R interval duration is the duration (i.e., length of time) between the R-wave detection and an R-wave detection that was one R-wave detection earlier.

Figure 3A:
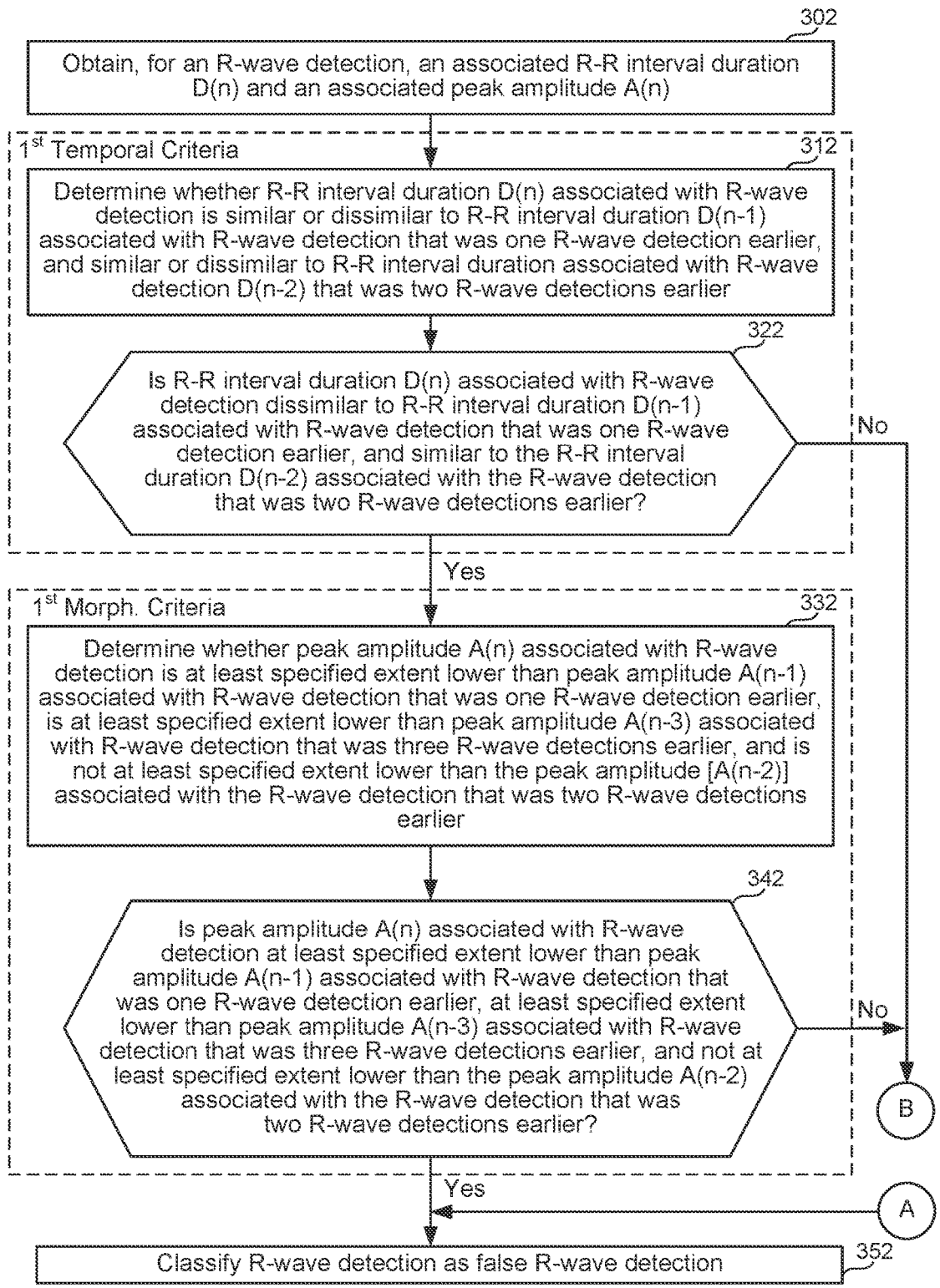
FIGS. 3A and 3B, which can be collectively referred to as FIG. 3, include a high level flow diagram that is used to describe a method for determining whether an R-wave detection should be classified as a false R-wave detection due to TWO or PWO, in accordance with certain embodiments of the present technology.
Figure 3B:
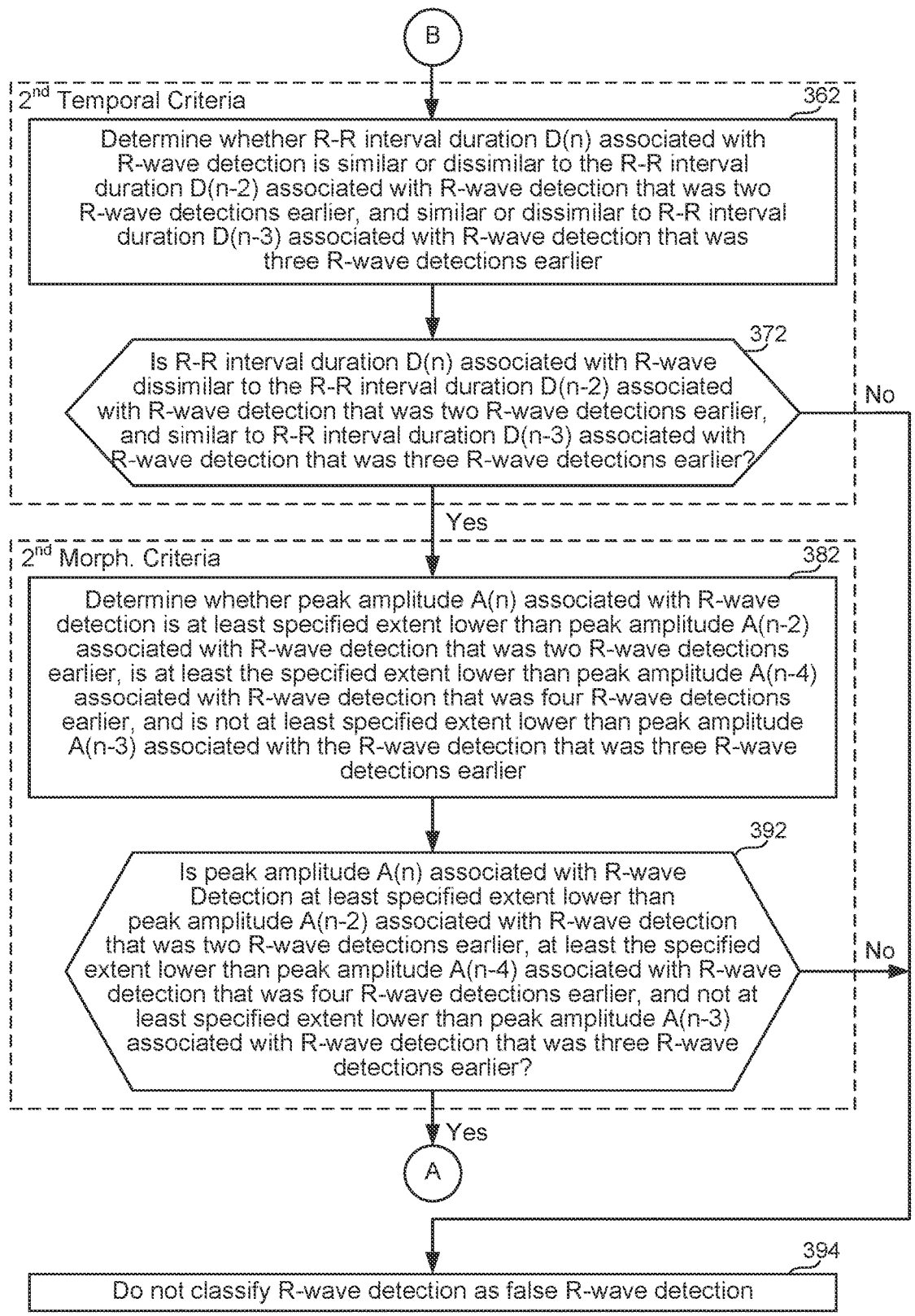

FIGS. 3A and 3B, which can be collectively referred to as FIG. 3, include a high level flow diagram that is used to describe a method for determining whether to classify an R-wave detection as a false R-wave detection in accordance with certain embodiments of the present technology.

Referring to FIG. 3A, step 302 involves obtaining for an R-wave detection, an associated R-R interval duration D(n) and an associated peak amplitude A(n). In an embodiment, the associated R-R interval duration D(n) is the duration between the R-wave detection and an R-wave detection that was one R-wave detection earlier. In an embodiment, the associated peak amplitude A(n) is a peak amplitude of an ECG or EGM signal within a window (e.g., a refractory window, but not limited thereto) that follows the R-wave detection. The associated R-R interval duration D(n) and the associated peak amplitude A(n), for an R-wave detection, can be determined by a processor of an IMD, and can be stored in memory (e.g., buffer memory) of the IMD so that it is available for use with the methods described herein, and/or other methods. Similarly, respective R-R interval durations and peak amplitudes can be determined and stored in memory for earlier detected (and later detected) R-wave detections, so that such durations and peak amplitudes are available for use with the methods described herein, and/or other methods.

Still referring to FIG. 3A, step 312 involves determining whether the R-R interval duration D(n) associated with the R-wave detection is similar or dissimilar to an R-R interval duration D(n−1) associated with an R-wave detection that was one R-wave detection earlier, and similar or dissimilar to an R-R interval duration associated with an R-wave detection D(n−2) that was two R-wave detections earlier. Step 322 involves determining whether the R-R interval duration D(n) associated with the R-wave detection is dissimilar to the R-R interval duration associated with the R-wave detection D(n−1) that was one R-wave detection earlier, and is similar to the R-R interval duration D(n−2) associated with the R-wave detection that was two R-wave detections earlier. If the answer to the determination at step 322 is Yes, that means the first TWO or PWO temporal criteria are met, and flow goes to steps 322 and 342 to determine whether the first TWO or PWO morphological criteria are met. If the answer to the determination at step 322 is No, that means the first TWO or PWO temporal criteria are not met, and flow goes to steps 362 and 372 in FIG. 3B to determine whether the second TWO or PWO temporal criteria and the second TWO or PWO morphological criteria are met. It is noted that while steps 312 and 322 are shown as two steps, these two steps can be combined into a single step. It is also noted that these steps can be made up of multiple sub-steps, as can be appreciated from FIG. 4A discussed below.

Still referring to FIG. 3A, steps 332 and 342 involve determining whether the peak amplitude A(n) associated with the R-wave detection is at least a specified extent lower than a peak amplitude A(n−1) associated with an R-wave detection that was one R-wave detection earlier, is at least the specified extent lower than a peak amplitude A(n−3) associated with an R-wave detection that was three R-wave detections earlier, and is not at least the specified extent lower than the peak amplitude A(n−2) associated with the R-wave detection that was two R-wave detections earlier. If the answer to the determination at step 342 is Yes, then it is determined that the first TWO or PWO morphological criteria are met, and flow goes to step 352 and the R-wave detection is classified as a false R-wave detection which is caused by TWO or PWO. If the answer to the determination at step 342 is No, that means the first TWO or PWO morphological criteria are not met, and flow goes to steps 362 and 372 in FIG. 3B to determine whether the second TWO or PWO temporal criteria and the second TWO or PWO morphological criteria are met. It is noted that while steps 332 and 342 are shown as two steps, these two steps can be combined into a single step. It is also noted that these steps can be made up of multiple sub-steps, as can be appreciated from FIG. 4A discussed below.

Referring now to FIG. 3B, step 362 involves determining whether the R-R interval duration D(n) associated with the R-wave detection is similar or dissimilar to the R-R interval duration D(n−2) associated with the R-wave detection that was two R-wave detections earlier, and similar or dissimilar to an R-R interval duration D(n−3) associated with an R-wave detection that was three R-wave detections earlier. Step 372 involves determining whether the R-R interval duration D(n) associated with the R-wave detection is dissimilar to the R-R interval duration D(n−2) associated with the R-wave detection that was two R-wave detections earlier, and similar to the R-R interval duration associated with the R-wave detection D(n−3) that was three R-wave detections earlier. If the answer to the determination at step 372 is Yes, then it is determined that the second TWO or PWO temporal criteria are met, and flow goes to steps 382 and 392, to determine whether the second TWO or PWO morphological criteria are met. It is noted that while steps 362 and 372 are shown as two steps, these two steps can be combined into a single step. It is also noted that these steps can be made up of multiple sub-steps, as can be appreciated from FIG. 4B discussed below. If the answer to the determination at step 372 is No, that means the second TWO or PWO temporal criteria are not met, and flow goes to step 394, at which the R-wave detection is not classified as a false R-wave detection.

Still referring to FIG. 3B, steps 382 and 392 involve determining whether the peak amplitude A(n) associated with the R-wave detection is at least the specified extent lower than the peak amplitude A(n−2) associated with an R-wave detection that was two R-wave detections earlier, is at least the specified extent lower than the peak amplitude A(n−4) associated with the R-wave detection that was four R-wave detections earlier, and is not at least the specified extent lower than the peak amplitude A(n−3) associated with the R-wave detection that was three R-wave detections earlier. If the answer to the determination at step 392 is Yes, that means the second TWO or PWO morphological criteria are met, flow goes to step 352 (in FIG. 3A), and the R-wave detection is classified as a false R-wave detection which is caused by P-wave or T-wave oversensing. If the answer to the determination at step 392 is No, that means the second TWO or PWO morphological criteria is not met, and flow goes to step 394, at which the R-wave detection is not classified as a false R-wave detection. It is noted that while steps 382 and 392 are shown as two steps, these two steps can be combined into a single step. It is also noted that these steps can be made up of multiple sub-steps, as can be appreciated from FIG. 4B discussed below. Further it is noted that steps 382 and 392 can be performed before steps 362 and 372, or more generally, that a determination of whether the second TWO or PWO morphological criteria are met can be performed prior to a determination of whether the second TWO or PWO temporal criteria are met.

Figure 4A:
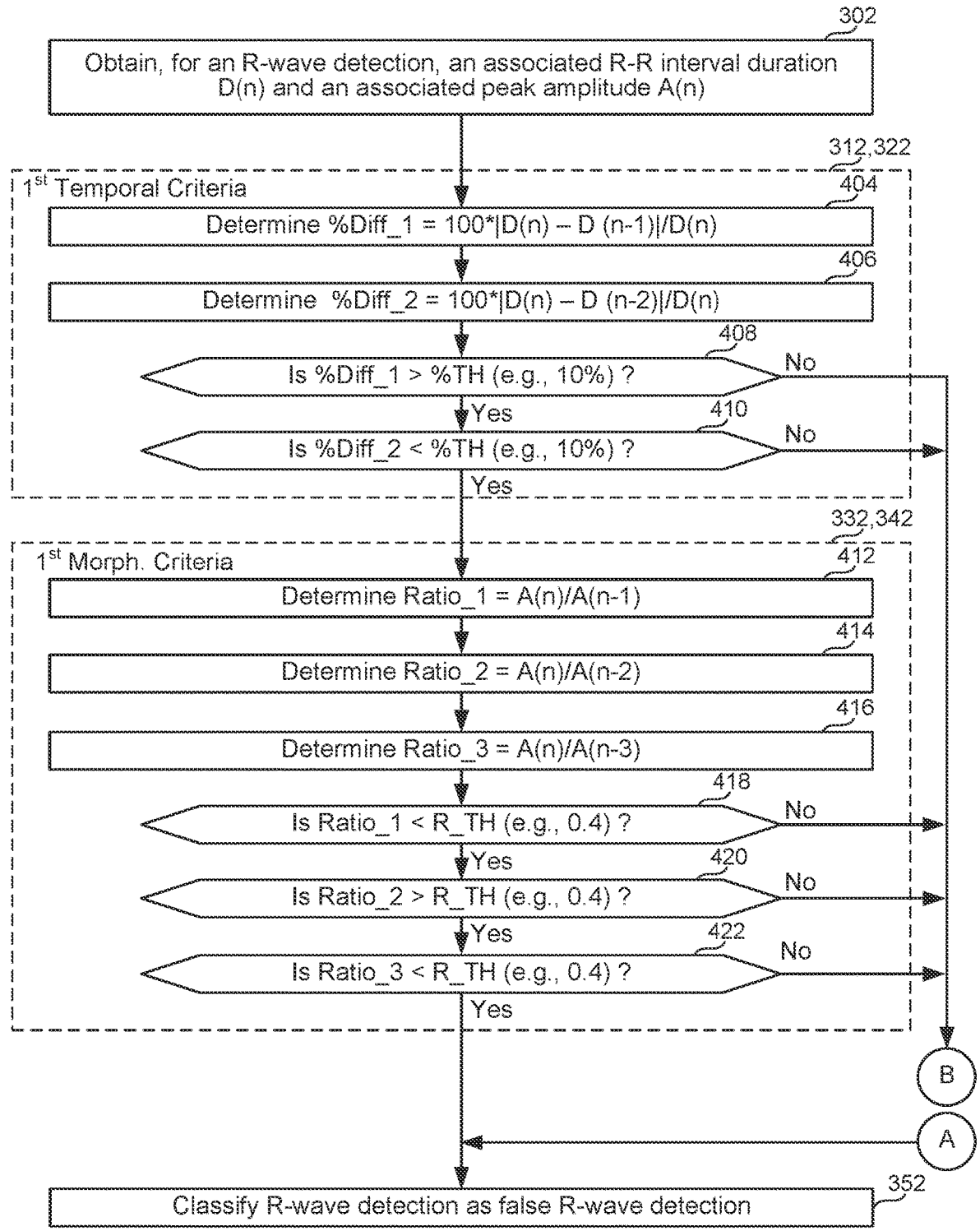
FIGS. 4A and 4B, which can be collectively referred to as FIG. 4, provides some additional details of how the method introduced with reference to FIG. 3 can be implemented in accordance with certain embodiments of the present technology.
Figure 4B:
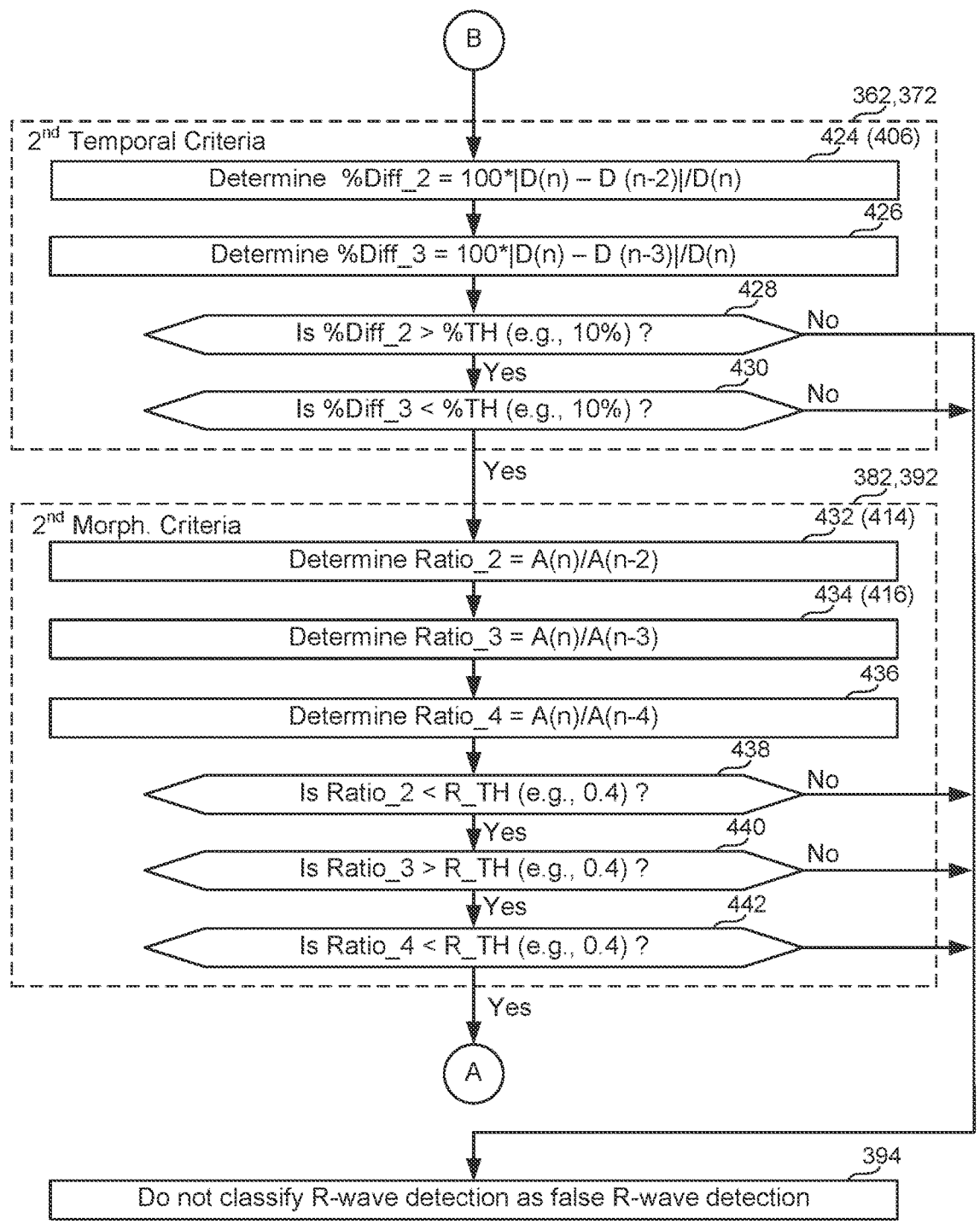

FIGS. 4A and 4B, which can be collectively referred to as FIG. 4, are now used provides some additional details of how the method introduced above with reference to FIG. 3 (which includes FIGS. 3A and 3B) can be implemented in accordance with certain embodiments of the present technology.

Referring to FIG. 4A, step 302 is the same as step 302 described above with reference to FIG. 3A, and thus need not be described again. Steps 404, 406, 408, and 410 can be used to perform steps 312 and 322 discussed above, and more generally, can be used to determine whether the first TWO or PWO temporal criteria are met. Step 404 involves determining a % Diff_1=100*|D(n)−D(n−1)|/D(n). Step 406 involves determining a % Diff_2=100*|D(n)−D(n−2)|/D(n). Step 408 involves determining whether the % Diff_1, i.e., 100*|D(n)−D(n−1)|/D(n), is greater than a specified percentage difference threshold, e.g., 10%. Step 410 involves determining whether the % Diff_2, i.e., 100*|D(n)−D(n−2)|/D(n), is less than the specified percentage difference threshold, e.g., 10%. If the answers to the determinations at steps 408 and 410 are both Yes, that means the first TWO or PWO temporal criteria are met, and then flow goes to steps 412 through 422, to determine whether the first TWO or PWO morphological criteria are met. If the answer to at least one of the determinations at step 408 and 410 is No, that means the first TWO or PWO temporal criteria are not met, and flow goes to 424-430 (in FIG. 4B) to determine whether the second TWO or PWO temporal criteria are met.

Steps 412 through 422 can be used to perform steps 332 and 342 discussed above, and more generally, can be used to determine whether the first TWO or PWO morphological criteria are met. Step 412 involves determining a Ratio_1=A(n)/A(n−1). Step 414 involves determining a Ratio_2=A(n)/A(n−2). Step 416 involves determining a Ratio_3=A(n)/A(n−3). Step 418 involves determining whether the Ratio_1<a ratio threshold (R_TH) (e.g., 0.4). Step 420 involves determining whether the Ratio_2>R_TH (e.g., 0.4). Step 422 involves determine whether the Ratio_3<R_TH (e.g., 0.4). If the answers to the determinations at steps 418, 420 and 422 are all Yes, that means the first TWO or PWO morphological criteria are met, and then flow goes to step 352. At step 352 the R-wave detection is classified as a false R-wave detection which is caused by P-wave or T-wave oversensing. If the answer to at least one of the determinations at step 418, 420 and 422 is No, that means the first TWO or PWO morphological criteria are not met, and flow goes to steps 424 through 430 (in FIG. 4B) to determine whether the second TWO or PWO temporal criteria are met.

Referring now to FIG. 4B, steps 424, 426, 428, and 430 can be used to perform steps 362 and 372 discussed above, and more generally, can be used to determine whether the second TWO or PWO temporal criteria are met. Step 424 involves determined a % Diff_2=100*|D(n)−D(n−2)|/D(n), which may have already been determined at step 406, and thus need not be determined again if the % Diff_2 was saved. Step 426 involves determining % Diff_3=100*|D(n)−D(n−3)|/D(n). Step 428 involves determining whether % Diff_2>% TH (e.g., 10%). Step 430 involves determining whether % Diff_3<% TH (e.g., 10%). If the answers to the determinations at steps 428 and 430 are both Yes, that means the second TWO or PWO temporal criteria are met, and then flow goes to steps 432 through 442, to determine whether the second TWO or PWO morphological criteria are met. If the answer to at least one of the determinations at step 428 and 430 is No, that means the second TWO or PWO temporal criteria are not met, and flow goes to step 394, at which the R-wave detection is not classified as a false R-wave detection.

Still referring to FIG. 4B, steps 432 through 442 can be used to perform steps 382 and 392 discussed above, and more generally, can be used to determine whether the second TWO or PWO morphological criteria are met. Step 432 involves determining a Ratio_2=A(n)/A(n−2), which may have already been determined at step 414, and thus need not be determined again if the Ratio_2 was saved. Step 434 involves determining a Ratio_3=A(n)/A(n−3), which may have already been determined at step 416, and thus need not be determined again if the Ratio_3 was saved. Step 436 involves determining a Ratio_4=A(n)/A(n−4). Step 438 involves determining whether the Ratio_2<R_TH (e.g., 0.4). Step 440 involves determining whether the Ratio_3>R_TH (e.g., 0.4). Step 422 involves determine whether the Ratio_4 <R_TH (e.g., 0.4). If the answers to the determinations at steps 438, 440 and 442 are all Yes, that means the second TWO or PWO morphological criteria are met, and then flow goes to step 352 (in FIG. 4A). At step 352 the R-wave detection is classified as a false R-wave detection which is caused by P-wave or T-wave oversensing. If the answer to at least one of the determinations at step 438, 440 and 442 is No, that means the second TWO or PWO morphological criteria are not met, and flow goes to step 394, at which the R-wave detection is not classified as a false R-wave detection.

In the embodiments described above with reference to FIGS. 3 and 4, an R-wave detection is classified as a false R-wave detection (caused by P-wave or T-wave oversensing) if either: the first TWO or PWO temporal criteria and the first TWO or PWO morphological criteria are both met; or if the second TWO or PWO temporal criteria and the second TWO or PWO morphological criteria are both met. In order to determine whether the first TWO or PWO temporal criteria or the second TWO or PWO temporal criteria are met, R-R interval durations associated with R-wave detections are compared to one another. The R-R interval durations are examples of temporal characteristics of the R-wave detections. In order to determine whether the first TWO or PWO morphological criteria or the second TWO or PWO morphological criteria are met, peak amplitudes associated with R-wave detections are compared to one another. The peak amplitudes are examples of morphological characteristics associated with the R-wave detections. As noted above, and explained in more detail below, in alternative embodiments other types of morphological characteristics associated with R-wave detections can be compared to one another instead of (or in addition to) peak amplitudes for the purpose of determining whether an R-wave detection should be classified as a false R-wave detection (caused by PWO or TWO).

Figure 5:
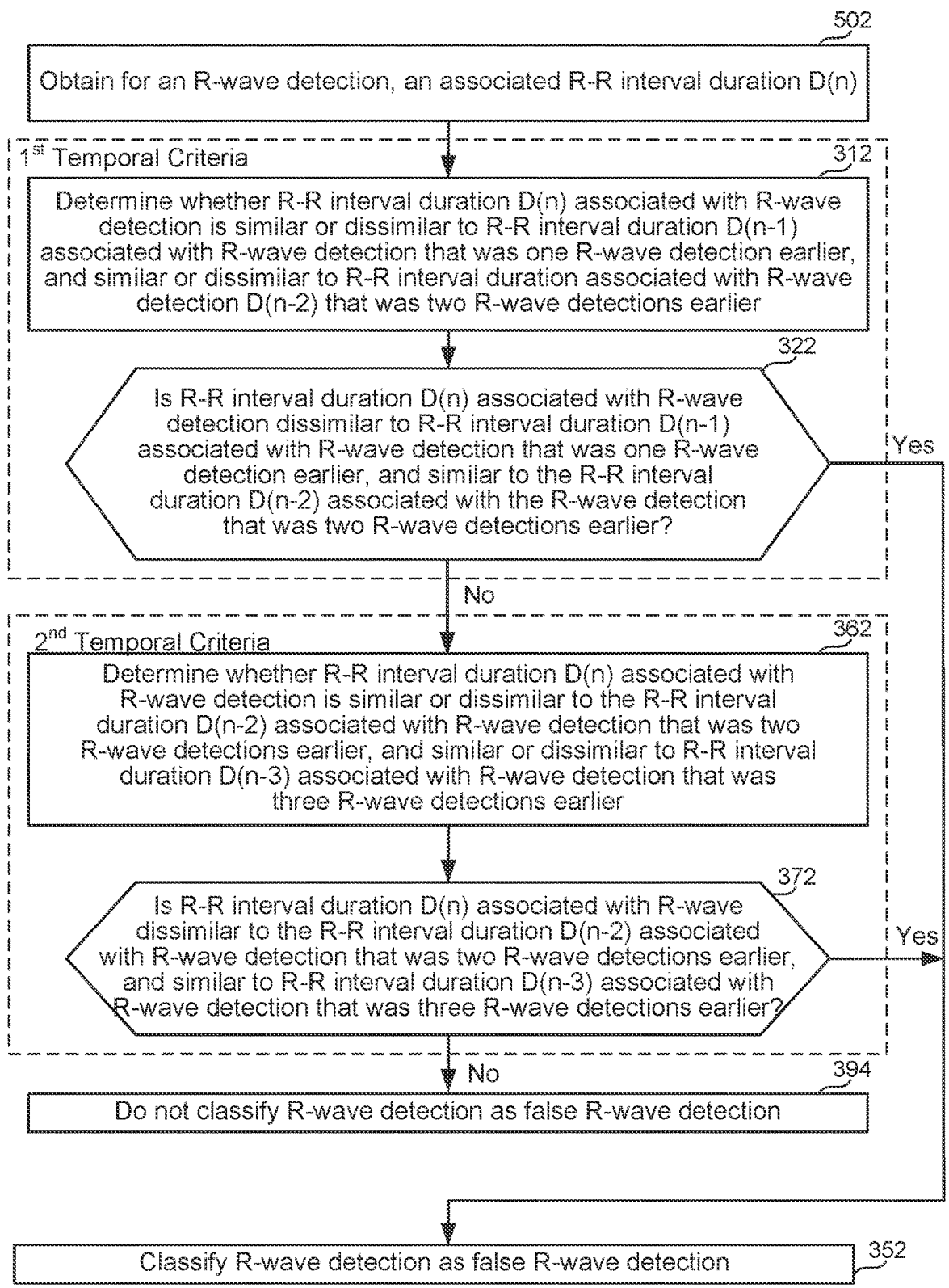
FIG. 5 includes a high level flow diagram that is used to describe how first and second TWO or PWO temporal criteria, can be used to determine whether an R-wave detection should be classified as a false R-wave detection, without using the first and second TWO or PWO morphological criteria.

In certain embodiments, which are less computationally intensive, but may have a lower positive predictive value, temporal characteristics of R-wave detections can be compared to one another, without comparing morphological characteristics of R-wave detections to one another, for the purpose of determining whether an R-wave detection should be classified as false R-wave detection (caused by P-wave or T-wave oversensing). For a more specific example, in accordance with certain embodiments, R-R interval durations associated with R-wave detections are compared to one another to determine whether one of the first TWO or PWO temporal criteria or the second TWO or PWO temporal criteria are met, and if so, then an R-wave detection is classified as a false R-wave detection (caused by PWO or TWO). An example high level flow diagram for such an embodiment is shown in FIG. 5. Referring to FIG. 5, step 502 involves obtaining an associated R-R interval duration D(n) for an R-wave detection. Steps 312 and 322 are used to determine whether the first TWO or PWO temporal criteria are met. If the first TWO or PWO temporal criteria are met, the answer to the determination at step 322 will be Yes, and the R-wave detection will be classified as a false R-wave detection at step 352. If the first TWO or PWO temporal criteria are not met, then steps 362 and 372 are used to determine whether the second TWO or PWO temporal criteria are met. If the second TWO or PWO temporal criteria are met, the answer to the determination at step 372 will be Yes, and the R-wave detection will be classified as a false R-wave detection at step 352. If neither the first TWO or PWO temporal criteria nor the second TWO or PWO temporal criteria are met, then the R-wave detection will not be classified as a false R-wave detection at step 394. Steps 312, 322, 352, 362, 372, and 394, which are shown in FIG. 5, were described above with reference to FIG. 3, and thus, need not be described again. Some additional example details of how these steps can be performed were described above with reference to FIG. 4.

Figure 6:
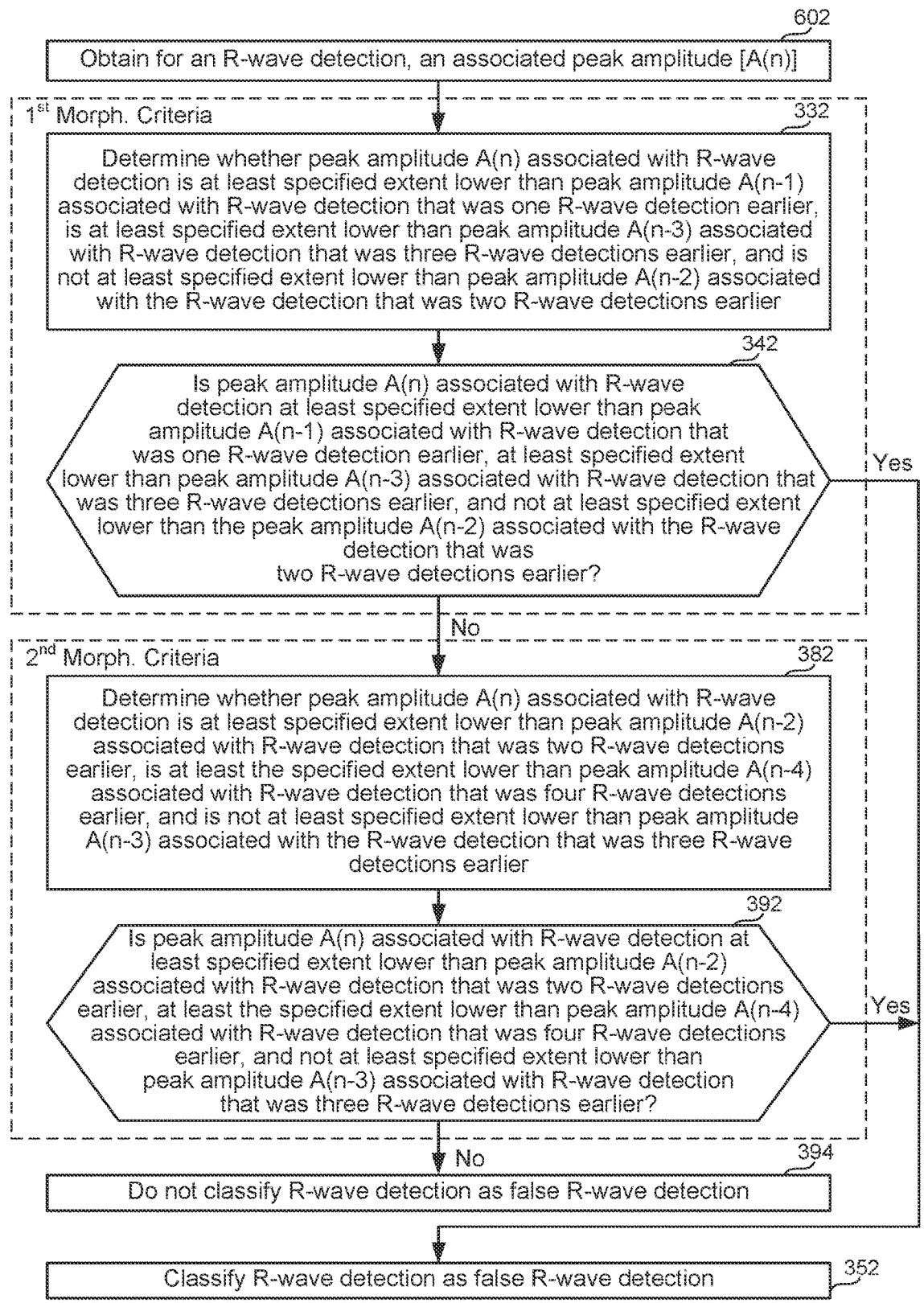
FIG. 6 includes a high level flow diagram that is used to describe how first and second TWO or PWO morphological temporal criteria can be used to determine whether an R-wave detection should be classified as a false R-wave detection, without using the first and second temporal TWO or PWO temporal criteria.

In certain other embodiments, which are less computationally intensive, but similarly may have a lower positive predictive value, morphological characteristics of R-wave detections can be compared to one another, without comparing temporal characteristics of R-wave detections to one another, for the purpose of determining whether an R-wave detection should be classified as false R-wave detection (caused by P-wave or T-wave oversensing). For a more specific example, in accordance with certain embodiments, peak amplitudes associated with R-wave detections are compared to one another to determine whether one of the first TWO or PWO morphological criteria or the second morphological criteria are met, and if so, then an R-wave detection is classified as a false R-wave detection (caused by P-wave or T-wave oversensing). An example high level flow diagram for such an embodiment is shown in FIG. 6. Referring to FIG. 6, step 602 involves obtaining an associated peak amplitude A(n) for an R-wave detection. Steps 332 and 342 are used to determine whether the first TWO or PWO morphological criteria are met. If the first morphological criteria are met, the answer to the determination at step 342 will be Yes, and the R-wave detection will be classified as a false R-wave detection at step 352. If the first TWO or PWO morphological criteria are not met, then steps 382 and 392 are used to determine whether the second TWO or PWO morphological criteria are met. If the second TWO or PWO morphological criteria are met, the answer to the determination at step 392 will be Yes, and the R-wave detection will be classified as a false R-wave detection at step 352. If neither the first TWO or PWO morphological criteria nor the second TWO or PWO morphological criteria are met, then the R-wave detection will not be classified as a false R-wave detection at step 394. Steps 332, 342, 352, 382, 392, and 394, which are shown in FIG. 6, were described above with reference to FIG. 3, and thus, need not be described again. Some additional example details of how these steps can be performed were described above with reference to FIG. 4.

Figure 7:
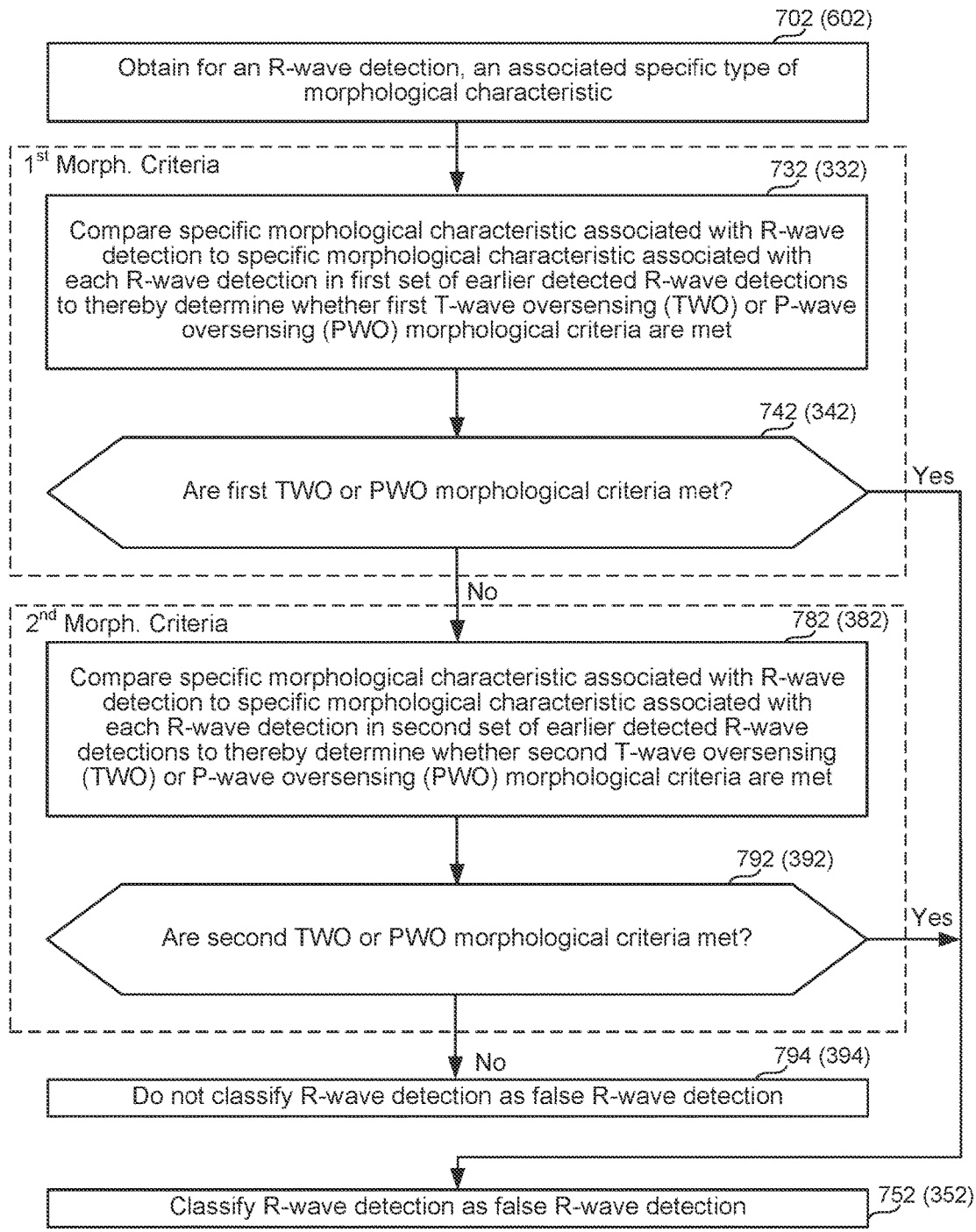
FIG. 7 includes another high level flow diagram that is used to describe how first and second TWO or PWO morphological criteria can be used to determine whether an R-wave detection should be classified as a false R-wave detection.

FIG. 7 includes a high level flow diagram that explains more generally how first and second TWO or PWO morphological criteria can be used to determine whether an R-wave detection should be classified as a false R-wave detection due to TWO or PWO. Referring to FIG. 7, step 702 involves obtaining, for an R-wave detection, an associated specific type of morphological characteristic. In accordance with specific embodiments, the specific type of morphological characteristic comprises peak amplitude. Where the specific type of morphological characteristic comprises peak amplitude, then step 702 is the same as step 602 described above. Alternative types of morphological characteristics that can be obtained at step 702 include, but are not limited to, an area under the curve (AUC) associated with the R-wave detection, a width (W) associated with the R-wave detection, or a maximum slope (MS) associated with the R-wave detection. The width (W) can be, e.g., a measure of a full width at R-wave threshold detection crossings, a full width at half maximum (FWHM), or a half width at half maximum (HWHM) associated with respective R-wave detections, but is not limited thereto. The maximum slope (MS) associated with an R-wave detection can be determined by determining a maximum derivative (dV/dt) of an ECG or EGM signal within a window surrounding or following the R-wave detection, as noted above. Such a window can be, e.g., a window that is from 50 milliseconds (msec) prior to the R-wave detection to 50 msec following the R-wave detection, but is not limited thereto.

Still referring to FIG. 7, step 732 involves comparing the specific morphological characteristic (e.g., peak amplitude) associated with the R-wave detection to the specific morphological characteristic associated with each R-wave detection in a first set of earlier detected R-wave detections to thereby determine whether first TWO or PWO morphological criteria are met. In certain embodiments, the first set of earlier detected R-wave detections includes R-wave detections that were one, two, and three R-wave detections earlier. Where the specific type of morphological characteristic comprises peak amplitude, and the first set of earlier detected R-wave detections includes R-wave detections that were one, two, and three R-wave detections earlier, then step 732 is the same as step 332 described above. At step 742 there is a determination of whether the first TWO or PWO morphological criteria are met. If the answer to the determination at step 742 is Yes, then flow goes to step 752, and the R-wave detection is classified as a false R-wave detection which is caused by TWO or PWO. If the answer to the determination at step 742 is No, then flow goes to step 782.

At step 782 involves comparing the specific morphological characteristic (e.g., peak amplitude) associated with the R-wave detection to the specific morphological characteristic associated with each R-wave detection in a second set of earlier detected R-wave detections to thereby determine whether the second TWO or PWO morphological criteria are met, wherein the second set differs from the first set but may have some overlap with the first set. In certain embodiments, the second set of earlier detected R-wave detections includes R-wave detections that were two, three, and four R-wave detections earlier. Where the specific type of morphological characteristic comprises peak amplitude, and the second set of earlier detected R-wave detections includes R-wave detections that were two, three and four R-wave detections earlier, then step 782 is the same as step 382 described above. At step 792 there is a determination of whether the second TWO or PWO morphological criteria are met. If the answer to the determination at step 792 is Yes, then flow goes to step 752, and the R-wave detection is classified as a false R-wave detection which is caused by TWO or PWO. If the answer to the determination at step 792 is No, then flow goes to step 794, and the R-wave detection is not classified as a false R-wave detection.

In accordance with certain embodiments, one of the above described techniques for determining whether an R-wave detection should be classified as a false R-wave detection (due TWO or PWO) can be performed in real time, such that each time an R-wave detection occurs, there is a determination whether the R-wave detection should be classified as a false R-wave detection prior to the next R-wave detection occurring. In certain such embodiments, whenever an R-wave detection occurs, there is a preliminary rhythm classification of the R-wave detection based on the R-R interval associated with the R-wave detection, and a marker for the preliminary classification (e.g., bradycardia, normal sinus rhythm, VT, or VF) can be produced and saved along with information about the R-wave detection, such as the associated R-R interval duration, peak amplitude, etc. The preliminary rhythm classification can be determined, for example, by determined which rate zone or R-R interval range the R-wave detection fits within, where there can be a separate rate zone or R-R interval range for each of a plurality of different rhythms, such as, but not limited to, normal sinus rhythm, bradycardia, VT, and VF. In certain IMDs, a type of arrhythmia (e.g., VT) will be detected (and potentially treated) in response to a threshold number of R-wave detections (within a specified amount of time, or within a specific number of R-wave detections) being classified as being that type of arrythmia (e.g., VT). For example, if 8 of the last 12 R-wave detections are classified as being VT type, then the IMD can detect a VT episode and deliver anti-tachycardia pacing (ATP) therapy to attempt to convert the VT episode to normal sinus rhythm. For another example, if 8 of the last 12 R-wave detections are classified as being VF type, then the IMD can detect a VF episode and deliver defibrillation shock therapy to attempt to convert the VF episode to normal sinus rhythm. This can be achieved, e.g., by incrementing an appropriate counter, such as a VT counter or a VF counter, in response to an R-wave detection being preliminarily classified as being a VT type or a VF type of rhythm. Where one of the above described techniques is used to classify an R-wave detection as a false R-wave detection (due TWO or PWO), then that R-wave detection may not be used to increment any of the aforementioned counters, the R-wave detection is binned as being unclassified, and/or the marker for the R-wave detection (e.g., a VT marker or VF marker) is discarded (aka trashed). Correcting such markers in real time is beneficial because it does not disturb arrythmia detection algorithms, and also improves downstream diagnostics.

In alternative embodiments, one of the above described techniques for determining whether an R-wave detection should be classified as a false R-wave detection (due TWO or PWO) can be performed after an arrhythmia is detected, to determine whether the arrhythmia detection should be rejected as likely being a false arrhythmia detection. For example, once VT is detected by an IMD, the IMD can analyze the R-wave detections within a window leading up to the VT detection to determine whether and/or to what extent the R-wave detections within the window were false R-wave detections. Then, if at least a threshold number of the R-wave detections are classified as being false R-wave detections, the arrythmia detection can be classified as a false arrythmia detection and treatment of the arrhythmia can be withheld. For a specific example implementation, an "oversensing score" can be calculated as the percent of R-wave detection events in the prescribed pre-detection window that are classified as over-sensed. If the "oversensing score" exceeds a threshold, then the arrhythmia detection can be rejected, and any therapy can be prevented or aborted. Other variations are also possible and within the scope of the embodiments described herein.

Alternatively, the R-wave detections that are classified as being false R-wave detections can be discarded, and one or more arrhythmia algorithms can be rerun to check whether the original arrythmia detection should be confirmed or rejected. For example, upon detection of an arrhythmia, a pre-detection window (e.g., a 30 second window leading up to the arrhythmia detection) is analyzed to determine if there were any over-sensed R-wave detection events within the pre-detection window. If one or more over-sensed events are identified, the over-sensed events can be discarded to produce a corrected pre-detection window. The corrected pre-detection window could then be analyzed to determine whether the arrythmia detection was likely a true positive or a false positive detection. In other words, whatever arrythmia detection algorithm(s) that were/was used to provide the initial arrhythmia detection can be re-run on the corrected pre-detection window. Other variations are also possible and within the scope of the embodiments described herein.

In accordance with certain embodiments of the present technology, an R-wave detection threshold and/or other types of R-wave sensing parameters can be adjusted based on whether and/or to what extend R-wave detections are classified as being false R-wave detections due to TWO or PWO. For example, if at least a threshold number of R-wave detections within a specified number of R-wave detections (or within a specified amount of time) are classified as being false R-wave detections due to PWO, then an R-wave detection threshold can be increased to reduce the chance of PWO. Alternatively, or additionally, if at least a threshold number of R-wave detections within a specified number of R-wave detections (or within a specified amount of time) are classified as being false R-wave detections due to TWO, then a delay decay of an R-wave detection threshold can be prolonged to reduce the chance of TWO, wherein the decay delay defines the interval at which a magnitude or sensitivity level of an R-wave detection threshold remains at a constant level following expiration of a refractory period before the R-wave detection threshold begins decreasing in real time. Other variations are also possible and within the scope of the embodiments described herein.

In accordance with certain embodiments of the present technology, PWO and/or TWO detection criteria can be dynamically adjusted based on whether and/or to what extend R-wave detections are classified as being false R-wave detections due to TWO or PWO. For example, one of the techniques described above can be performed in real time for the most recently detected R-wave detection, and one or more histograms can be generated to track R-T interval variation and T-wave amplitude variation. Then, when a newly detected R-wave detection has an associated R-R interval duration and an associated peak amplitude (and/or some other morphological characteristic) within the range of one of the generated histograms, the R-wave detection criteria may be adjusted because it is more likely that the R-wave detection is another TWO or PWO event. Other variations are also possible and within the scope of the embodiments described herein.

In accordance with certain embodiments, an IMD may perform one of the methods described above with reference to FIGS. 3 through 7 in response to an arrhythmic episode being detected. The detection of an arrhythmia episode can also be referred to as an arrhythmia trigger. Such an IMD may be configured to transmit, to an external device that is communicatively coupled to a patient care network, data corresponding to the arrhythmic episode that is detected by the IMD. In certain such embodiments, the IMD does not (is prevented from) transmitting (to the external device that is communicatively coupled to the patient care network) data corresponding to an arrhythmic episode that is detected by the IMD, but is thereafter determined by the IMD as being a false positive detection.

In accordance with certain embodiments, the medical device (e.g., IMD) that performs one of the methods described above with reference to FIGS. 3 through 7 may monitor the HR of a patient based on intervals identified from a segment of an EGM or ECG, and the medical device can determine based on the results of the method whether a monitored HR is inaccurate due to oversensing and thus should be ignored or recalculated. For an example, if an oversensing score exceeds a corresponding threshold, the medical device can conclude that a HR that was determined based on sensed interval is inaccurate and should not be used, or should be recalculated.

Embodiments of the present technology described herein can be used with various types of IMDs, including, but not limited to, an insertable cardiac monitor (ICM), a cardiac pacemaker to which one or more leads is/are attached, a leadless cardiac pacemaker (LCP), or an implantable cardioverter defibrillator (ICD). Such an ICD can be a transvascular ICD, or a nonvascular ICD, wherein the nonvascular ICD can be a subcutaneous (SubQ) ICD. Where embodiments of the present technology are implemented by an ICM, such embodiments can be used, e.g., to reduce the number of false positive AF detections that are transmitted from the ICM to a patient care network for clinician review. This is beneficially because false positive AF detections are highly undesirable, as the burden of sorting through large numbers of clinically irrelevant episodes of AF can be time consuming and costly. Where embodiments of the present technology are used by an ICD, or by an IMD in communication with an ICD, such embodiments can reduce how often anti-tachycardia pacing (ATP) and/or defibrillation shocks are delivered in response to false positive tachycardia detections. This is beneficial because defibrillation shocks are typically painful, and delivering such shocks when patient is awake in response to false positive tachycardia detections subjects the patient to unnecessary painful or uncomfortable shocks and may prematurely deplete the energy stored in a battery.

Figure 8:
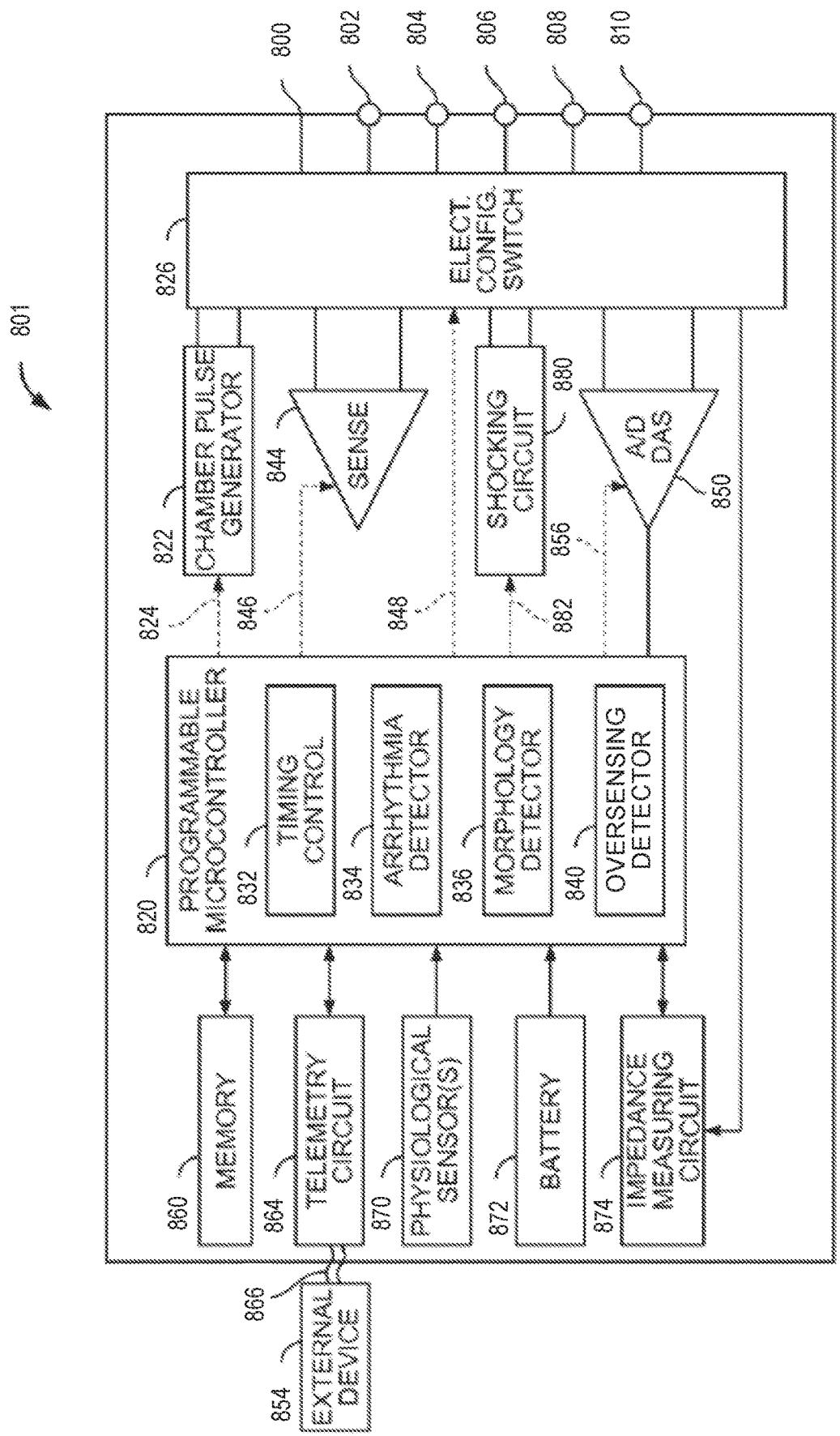
FIG. 8 shows a block diagram of one embodiment of an IMD that is implanted into a patient in accordance with certain embodiments of the present technology.

FIG. 8 shows a block diagram of one embodiment of an IMD that is implanted into a patient in accordance with a certain embodiment of the present technology. The IMD 801 may be implemented as a full-function biventricular pacemaker, equipped with both atrial and ventricular sensing and pacing circuitry for four chamber sensing and stimulation therapy (including both pacing and shock treatment). Optionally, the IMD 801 may provide full-function cardiac resynchronization therapy. Alternatively, the IMD 801 may be implemented with a reduced set of functions and components. For instance, the IMD may be implemented without pacing, e.g., if the IMD is an ICM. The IMD 801 can be coupled to one or more leads for single chamber or multi-chamber pacing and/or sensing. Alternatively, the IMD 801 can be an LCP that includes electrodes located on or very close to a housing 800 of the IMD 801.

The IMD 801 has a housing 800 to hold the electronic/computing components. The housing 800 (which is often referred to as the "can", "case", "encasing", or "case electrode") may be programmably selected to act as the return electrode for certain stimulus modes. The housing 800 may further include a connector (not shown) with a plurality of terminals 802, 804, 806, 808, and 810. The terminals may be connected to electrodes that are located in various locations on the housing 800 or to electrodes located on leads. The electrodes to which the terminals 802, 804, 806, 808, and 810 are connected can also be referenced, respectively, using reference numbers 802, 804, 806, 808, and 810, and the case electrode can be referenced as case electrode 800. The IMD 801 includes a programmable microcontroller 820 that controls various operations of the IMD 801, including cardiac monitoring and/or stimulation therapy. The microcontroller 820 includes a microprocessor (or equivalent control circuitry), RAM and/or ROM memory, logic and timing circuitry, state machine circuitry, and I/O circuitry.

The IMD 801 further includes a pulse generator 822 that generates stimulation pulses and communication pulses for delivery by two or more electrodes coupled thereto. The pulse generator 822 is controlled by the microcontroller 820 via a control signal 824. The pulse generator 822 may be coupled to the select electrode(s) via an electrode configuration switch 826, which includes multiple switches for connecting the desired electrodes to the appropriate I/O circuits, thereby facilitating electrode programmability. The switch 826 is controlled by a control signal 828 from microcontroller 820.

In the embodiment of FIG. 8, a single pulse generator 822 is illustrated. Optionally, the IMD may include multiple pulse generators, similar to the pulse generator 822, where each pulse generator is coupled to two or more electrodes and controlled by the microcontroller 820 to deliver select stimulus pulse(s) to the corresponding two or more electrodes.

The microcontroller 820 is illustrated as including timing control circuitry 832 to control the timing of the stimulation pulses (e.g., pacing rate, atrio-ventricular (AV) delay, atrial interconduction (A-A) delay, or ventricular interconduction (V-V) delay, etc.). The timing control circuitry 832 may also be used for the timing of refractory periods, blanking intervals, noise detection windows, evoked response windows, alert intervals, marker channel timing, and so on. The microcontroller 820 also has an arrhythmia detector 834 for detecting arrhythmia conditions and a morphology detector 836. Although not shown, the microcontroller 820 may further include other dedicated circuitry and/or firmware/software components that assist in monitoring various conditions of the patient's heart and managing pacing therapies. The microcontroller 820 is also shown as including an oversensing detector 840, which can be used to perform any of the embodiments of the present technology described above with reference to FIGS. 1-7. The oversensing detector 840 can more generally be implemented using hardware, software, firmware, and/or combinations thereof. The microcontroller can include a processor. The microcontroller, and/or the processor thereof, can be used to perform the methods of the present technology described herein.

The IMD 801 can be further equipped with a communication modem (modulator/demodulator) to enable wireless communication with the remote slave pacing unit. The modem may include one or more transmitters and two or more receivers. In one implementation, the modem may use low or high frequency modulation. As one example, modem may transmit implant-to-implant (i2i) messages and other signals through conductive communication between a pair of electrodes. Such a modem may be implemented in hardware as part of the microcontroller 820, or as software/firmware instructions programmed into and executed by the microcontroller 820. Alternatively, the modem may reside separately from the microcontroller as a standalone component.

The IMD 801 includes a sensing circuit 844 selectively coupled to two or more electrodes, that perform sensing operations, through the switch 826 to detect the presence of cardiac activity in the right chambers of the heart. The sensing circuit 844 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. The switch 826 determines the sensing polarity of the cardiac signal by selectively closing the appropriate switches. In this way, the clinician may program the sensing polarity independent of the stimulation polarity.

The output of the sensing circuit 844 is connected to the microcontroller 820 which, in turn, triggers or inhibits the pulse generator 822 in response to the presence or absence of cardiac activity. The sensing circuit 844 receives a control signal 846 from the microcontroller 820 for purposes of controlling the gain, threshold, polarization charge removal circuitry (not shown), and the timing of any blocking circuitry (not shown) coupled to the inputs of the sensing circuitry.

In the embodiment of FIG. 8, a single sensing circuit 844 is illustrated. Optionally, the IMD may include multiple sensing circuits, similar to the sensing circuit 844, where each sensing circuit is coupled to two or more electrodes and controlled by the microcontroller 820 to sense electrical activity detected at the corresponding two or more electrodes. The sensing circuit 844 may operate in a unipolar sensing configuration or in a bipolar sensing configuration.

The IMD 801 further includes an analog-to-digital (ND) data acquisition system (DAS) 850 coupled to two or more electrodes via the switch 826 to sample cardiac signals across any pair of desired electrodes. Data acquisition system 850 is configured to acquire intracardiac electrogram signals, convert the raw analog data into digital data, and store the digital data for later processing and/or telemetric transmission to an external device 854 (e.g., a programmer, local transceiver, or a diagnostic system analyzer). Data acquisition system 850 is controlled by a control signal 856 from the microcontroller 820.

The microcontroller 820 is coupled to a memory 860 by a suitable data/address bus. The programmable operating parameters used by the microcontroller 820 are stored in memory 860 and used to customize the operation of the IMD 801 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of the IMD 801 may be non-invasively programmed into memory 860 through a telemetry circuit 864 in telemetric communication via a communication link 866 with an external device 854. The telemetry circuit 864 allows intracardiac electrograms and status information relating to the operation of the IMD 801 (as contained in the microcontroller 820 or memory 860) to be sent to the external device 854 through the communication link 866.

The IMD 801 can further include magnet detection circuitry (not shown), coupled to the microcontroller 820, to detect when a magnet is placed over the unit. A magnet may be used by a clinician to perform various test functions of IMD 801 and/or to signal the microcontroller 820 that the external device 854 is in place to receive or transmit data to the microcontroller 820 through the telemetry circuit 864.

The IMD 801 can further include one or more physiological sensors 870. Such sensors are commonly referred to as "rate-responsive" sensors because they are typically used to adjust pacing stimulation rates according to the exercise state of the patient. However, the physiological sensor(s) 870 may further be used to detect changes in cardiac output, changes in the physiological condition of the heart, or diurnal changes in activity (e.g., detecting sleep and wake states). Signals generated by the physiological sensor(s) 870 are passed to the microcontroller 820 for analysis. The microcontroller 820 responds by adjusting the various pacing parameters (such as rate, AV Delay, V-V Delay, etc.) at which the atrial and ventricular pacing pulses are administered. While shown as being included within the IMD 801, one or more physiological sensor(s) 870 may be external to the IMD 801, yet still be implanted within or carried by the patient. Examples of physiologic sensors include sensors that, for example, sense respiration rate, pH of blood, ventricular gradient, activity, position/posture, minute ventilation (MV), and so forth.

A battery 872 provides operating power to all of the components in the IMD 801. The battery 872 is preferably capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 872 also desirably has a predictable discharge characteristic so that elective replacement time can be detected. As one example, the IMD 801 employs lithium/silver vanadium oxide batteries.

The IMD 801 further includes an impedance measuring circuit 874, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 874 is coupled to the switch 826 so that any desired electrode may be used. In this embodiment the IMD 801 further includes a shocking circuit 880 coupled to the microcontroller 820 by a data/address bus 882.

The embodiments of the present technology described above were primarily described as being used with an implantable medical device or system that monitors HR and/or for one or more types of arrhythmic episodes based on sensed intervals, which as noted above can be, e.g., true R-R intervals or over-sensed R-R intervals. Such embodiments of the present technology can alternatively be used with a non-implantable device or system (aka an external device or system) that includes at least two electrodes in contact with a person's skin and is used to monitor HR and/or for one or more types of arrhythmic episodes based on sensed intervals. More specifically, such embodiments can alternatively be used with or be implemented by a user wearable device, such as a wrist worn device, or a user wearable device designed to be worn on one or more other portions of a person's body besides a wrist, e.g., on an ankle, an upper arm, or a chest, but not limited thereto. Such a user wearable device can include electrodes that are configured to contact a person's skin, sensing circuity coupled to the electrodes and configured to obtain a signal indicative of electrical activity of a patient's heart, and at least one of a processor or controller that is configured to perform one or more of the algorithms described above. Such a user wearable device (or more generally an external device or system) can monitor for AF and/or other types of arrythmia(s) and determine when there is a false positive detection. Additionally, or alternatively, such a user wearable device (or more generally an external device or system) can monitor a person's HR and determine when measures of HR are likely inaccurate due to oversensing. A user wearable device can both obtain a signal indicative of electrical activity of a patient's heart and monitor a person's HR and/or for arrythmia(s) based on intervals obtained from the obtained signal. Alternatively, a user wearable device can be communicatively coupled to another external device, such as a smartphone or tablet computer, and the other external device can obtain the signal from the user wearable device and monitor a person's HR and/or for arrythmia(s) based on intervals. The user wearable device or other external device or system can determine when there may be a false positive and/or when a measured HR may be inaccurate due to oversensing. Other implementations of such an external device or system are also possible and within the scope of the embodiments described herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 2 through 7. It would also be possible to recorder some of the steps shown in FIGS. 3 through 7. For another example, it is possible to change the boundaries of some of the blocks shown in FIG. 8.

The specific thresholds (e.g., percentage threshold, ratio thresholds, specified extents less then, etc.) mentioned above were just provided as examples and can be systematically optimized for a broader patient population, or for individual patients. Accordingly, embodiments of the present technology described herein should not be limited to use with the exemplary thresholds described herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for use by an implantable medical device (IMD), the method comprising:

sensing a signal indicative of electrical activity of a patient's heart;

detecting R-waves based on comparisons of the signal indicative of electrical activity of the patient's heart, or samples thereof, to an R-wave detection threshold;

detecting an arrhythmic episode based on the R-wave detections;

in response to the arrhythmic episode detection, for each R-wave detection of at least some of the R-wave detections in a window leading up to the arrhythmic episode detection, determining whether the R-wave detection should be classified as a false R-wave detection due to T-wave oversensing (TWO) or P-wave oversensing (PWO) by:

comparing a specific morphological characteristic associated with the R-wave detection to the specific morphological characteristic associated with each R-wave detection in a first set of earlier detected R-wave detections including R-wave detections that were one, two, and three R-wave detections earlier to thereby determine whether first TWO or PWO morphological criteria are met, and in a second set of earlier detected R-wave detections including R-wave detections that were two, three, and four R-wave detections earlier to thereby determine whether second TWO or PWO morphological criteria are met, wherein the second set differs from the first set but has some overlap with the first set; and classifying the R-wave detection as a false R-wave detection based on whether one of the first or second TWO or PWO morphological criteria being met; and based on an extent of the R-wave detections classified as being false R-wave detections due to TWO or PWO, performing at least one of: selectively preventing or aborting delivery of therapy by the IMD intended to treat the arrhythmic episode; selectively preventing transmission by the IMD to an external device of data corresponding to the arrhythmic episode that can be used for diagnostic purposes; or selectively adjusting at least one parameter of the R-wave detection threshold that can be used by the IMD for detecting further R-waves and thereby detecting a further arrhythmic episode.

2. The method of claim 1, wherein:

the specific morphological characteristic comprises a peak amplitude (A);

the first TWO or PWO morphological criteria are met when a peak amplitude A (n) associated with the R-wave detection is at least a specified extent lower than a peak amplitude A (n−1) associated with the R-wave detection that was one R-wave detection earlier, is not at least the specified extent lower than a peak amplitude A (n−2) associated with the R-wave detection that was two R-wave detections earlier, and is at least the specified extent lower than a peak amplitude A (n−3) associated with the R-wave detection that was three R-wave detections earlier; and the second TWO or PWO morphological criteria are met when the peak amplitude A (n) associated with the R-wave detection is at least the specified extent lower than the peak amplitude A (n−2) associated with the R-wave detection that was two R-wave detections earlier, is not at least the specified extent lower than the peak amplitude A (n−3) associated with the R-wave detection that was three R-wave detections earlier, and is at least the specified extent lower than a peak amplitude A (n−4) associated with the R-wave detection that was four R-wave detections earlier.

3. The method of claim 1, wherein:

the specific morphological characteristic comprises an area under the curve (AUC);

the first TWO or PWO morphological criteria are met when an AUC (n) associated with the R-wave detection is at least a specified extent less than an AUC (n−1) associated with the R-wave detection that was one R-wave detection earlier, is not at least the specified extent less than an AUC (n−2) associated with the R-wave detection that was two R-wave detections earlier, and is at least the specified extent less than an AUC (n−3) associated with the R-wave detection that was three R-wave detections earlier; and the second TWO or PWO morphological criteria are met when the AUC (n) associated with the R-wave detection is at least the specified extent less than the AUC (n−2) associated with the R-wave detection that was two R-wave detections earlier, is not at least the specified extent less than the AUC (n−3) associated with the R-wave detection that was three R-wave detections earlier, and is at least the specified extent less than an AUC (n−4) associated with the R-wave detection that was four R-wave detections earlier.

4. The method of claim 1, wherein:

the specific morphological characteristic comprises a width (W);

the first TWO or PWO morphological criteria are met when a width W (n) associated with the R-wave detection is at least a specified extent longer than a width W (n−1) associated with the R-wave detection that was one R-wave detection earlier, is not at least the specified extent longer than a width W (n−2) associated with the R-wave detection that was two R-wave detections earlier, and is at least the specified extent longer than a width W (n−3) associated with the R-wave detection that was three R-wave detections earlier;

the second TWO or PWO morphological criteria are met when the width W (n) associated with the R-wave detection is at least the specified extent longer than the width W (n−2) associated with the R-wave detection that was two R-wave detections earlier, is not at least the specified extent longer than the width W (n−3) associated with the R-wave detection that was three R-wave detections earlier, and is at least the specified extent longer than a width W (n−4) associated with the R-wave detection that was four R-wave detections earlier; and each said width can be a measure of a full width at a crossing of the R-wave detection threshold, a full width at half maximum (FWHM), or a half width at half maximum (HWHM) associated with respective R-wave detections.

5. The method of claim 1, wherein:

the specific morphological characteristic comprises a maximum slope (MS);

the first TWO or PWO morphological criteria are met when a MS (n) associated with the R-wave detection is at least a specified extent less than an MS (n−1) associated with the R-wave detection that was one R-wave detection earlier, is not at least the specified extent less than an MS (n−2) associated with the R-wave detection that was two R-wave detections earlier, and is at least the specified extent less than an MS (n−3) associated with the R-wave detection that was three R-wave detections earlier; and the second TWO or PWO morphological criteria are met when the MS (n) associated with the R-wave detection is at least the specified extent less than the MS (n−2) associated with the R-wave detection that was two R-wave detections earlier, is not at least the specified extent less than the MS (n−3) associated with the R-wave detection that was three R-wave detections earlier, and is at least the specified extent less than an MS (n−4) associated with the R-wave detection that was four R-wave detections earlier.

6. The method of claim 1, further comprising:

comparing an R-R interval duration associated with the R-wave detection to an R-R interval duration associated with each R-wave detection in a third set of earlier detected R-wave detections to thereby determine whether first TWO or PWO temporal criteria are met, and in a fourth set of earlier detected R-wave detections to thereby determine whether second TWO or PWO temporal criteria are met, wherein the fourth set differs from the third set but has some overlap with the third set; and classifying the R-wave detection as a false R-wave detection, is also based on one of the first or the second TWO or PWO temporal criteria are met.

7. The method of claim 6, wherein:

the third set of earlier detected R-wave detections includes the R-wave detections that were one and two R-wave detections earlier;

the fourth set of earlier detected R-wave detections includes the R-wave detections that were two and three R-wave detections earlier;

the first TWO or PWO temporal criteria are met when an R-R interval duration D (n) associated with the R-wave detection is dissimilar to an R-R interval duration D (n−1) associated with the R-wave detection that was one R-wave detection earlier, and is similar to an R-R interval duration D (n−2) associated with the R-wave detection that was two R-wave detections earlier; and the second TWO or PWO temporal criteria are met when the R-R interval duration D (n) associated with the R-wave detection is dissimilar to the R-R interval duration D (n−2) associated with the R-wave detection that was two R-wave detections earlier, and is similar to an R-R interval duration D (n−3) associated with the R-wave detection that was three R-wave detections earlier.

8. The method of claim 7, wherein the classifying the R-wave detection as a false R-wave detection, comprises classifying the R-wave detection as a false R-wave detection in response to:

both the first TWO or PWO morphological criteria and the first TWO or PWO temporal criteria being met; or both the second TWO or PWO morphological criteria and the second TWO or PWO temporal criteria being met.

9. An implantable medical device (IMD), comprising:

two or more electrodes;

a sensing circuit coupled to at least two of the two or more electrodes and configured to obtain a signal indicative of electrical activity of a patient's heart; and a processor or controller configured to detect an arrhythmic episode based on R-wave detections that are detected based on comparisons of the signal indicative of electrical activity of the patient's heart, or samples thereof, to an R-wave detection threshold;

wherein in response to the arrhythmic episode detection, for each R-wave detection of at least some of the R-wave detections in a window leading up to the arrhythmic episode detection, in order to determine whether the R-wave detection should be classified as a false R-wave detection due to T-wave oversensing (TWO) or P-wave oversensing (PWO), the processor or controller is configured to compare a specific morphological characteristic associated with the R-wave detection to the specific morphological characteristic associated with each R-wave detection in a first set of earlier detected R-wave detections including R-wave detections that were one, two, and three R-wave detections earlier to thereby determine whether first TWO or PWO morphological criteria are met, and in a second set of earlier detected R-wave detections including R-wave detections that were two, three, and four R-wave detections earlier to thereby determine whether second TWO or PWO morphological criteria are met, wherein the second set differs from the first set but has some overlap with the first set; and classify the R-wave detection as a false R-wave detection based on one of the first or second TWO or PWO morphological criteria being met; and wherein based on an extent of the R-wave detections classified as being false R-wave detections due to TWO or PWO, the processor or controller is configured to at least one of: selectively prevent or abort delivery of therapy by the IMD intended to treat the arrhythmic episode; selectively prevent transmission by the IMD to an external device of data corresponding to the arrhythmic episode that can be used for diagnostic purposes; or selectively adjust at least one parameter of the R-wave detection threshold that can be used by the IMD to detect further R-waves and thereby detect a further arrhythmic episode.

10. The IMD of claim 9, wherein:

the specific morphological characteristic comprises a peak amplitude (A);

the processor or controller is configured to determine that the first TWO or PWO morphological criteria are met when a peak amplitude A (n) associated with the R-wave detection is at least a specified extent lower than a peak amplitude A (n−1) associated with the R-wave detection that was one R-wave detection earlier, is not at least the specified extent lower than a peak amplitude A (n−2) associated with the R-wave detection that was two R-wave detections earlier, and is at least the specified extent lower than a peak amplitude A (n−3) associated with the R-wave detection that was three R-wave detections earlier; and the processor or controller is configured to determine that the second TWO or PWO morphological criteria are met when the peak amplitude A (n) associated with the R-wave detection is at least the specified extent lower than the peak amplitude A (n−2) associated with the R-wave detection that was two R-wave detections earlier, is not at least the specified extent lower than the peak amplitude A (n−3) associated with the R-wave detection that was three R-wave detections earlier, and is at least the specified extent lower than a peak amplitude A (n−4) associated with the R-wave detection that was four R-wave detections earlier.

11. The IMD of claim 9, wherein:

the specific morphological characteristic comprises an area under the curve (AUC);

the processor or controller is configured to determine that the first TWO or PWO morphological criteria are met when an AUC (n) associated with the R-wave detection is at least a specified extent less than an AUC (n−1) associated with the R-wave detection that was one R-wave detection earlier, is not at least the specified extent less than an AUC (n−2) associated with the R-wave detection that was two R-wave detections earlier, and is at least the specified extent less than an AUC (n−3) associated with the R-wave detection that was three R-wave detections earlier; and the processor or controller is configured to determine that the second TWO or PWO morphological criteria are met when the AUC (n) associated with the R-wave detection is at least the specified extent less than the AUC (n−2) associated with the R-wave detection that was two R-wave detections earlier, is not at least the specified extent less than the AUC (n−3) associated with the R-wave detection that was three R-wave detections earlier, and is at least the specified extent less than an AUC (n−4) associated with the R-wave detection that was four R-wave detections earlier.

12. The IMD of claim 9, wherein:

the specific morphological characteristic comprises a width (W);

the processor or controller is configured to determine that the first TWO or PWO morphological criteria are met when a width W (n) associated with the R-wave detection is at least a specified extent longer than a width W (n−1) associated with the R-wave detection that was one R-wave detection earlier, is not at least the specified extent longer than a width W (n−2) associated with the R-wave detection that was two R-wave detections earlier, and is at least the specified extent longer than a width W (n−3) associated with the R-wave detection that was three R-wave detections earlier;

the processor or controller is configured to determine that the second TWO or PWO morphological criteria are met when the width W (n) associated with the R-wave detection is at least the specified extent longer than the width W (n−2) associated with the R-wave detection that was two R-wave detections earlier, is not at least the specified extent longer than the width W (n−3) associated with the R-wave detection that was three R-wave detections earlier, and is at least the specified extent longer than a width W (n−4) associated with the R-wave detection that was four R-wave detections earlier; and each said width can be a measure of a full width at a crossing of the R-wave detection threshold, a full width at half maximum (FWHM), or a half width at half maximum (HWHM) associated with respective R-wave detections.

13. The IMD of claim 9, wherein:

the specific morphological characteristic comprises a maximum slope (MS);

the processor or controller is configured to determine that the first TWO or PWO morphological criteria are met when a MS (n) associated with the R-wave detection is at least a specified extent less than an MS (n−1) associated with the R-wave detection that was one R-wave detection earlier, is not at least the specified extent less than an MS (n−2) associated with the R-wave detection that was two R-wave detections earlier, and is at least the specified extent less than an MS (n−3) associated with the R-wave detection that was three R-wave detections earlier; and the processor or controller is configured to determine that the second TWO or PWO morphological criteria are met when the MS (n) associated with the R-wave detection is at least the specified extent less than the MS (n−2) associated with the R-wave detection that was two R-wave detections earlier, is not at least the specified extent less than the MS (n−3) associated with the R-wave detection that was three R-wave detections earlier, and is at least the specified extent less than an MS (n−4) associated with the R-wave detection that was four R-wave detections earlier.

14. The IMD of claim 9, wherein the processor or controller is further configured to:

compare an R-R interval duration associated with the R-wave detection to an R-R interval duration associated with each R-wave detection in a third set of earlier detected R-wave detections to thereby determine whether first TWO or PWO temporal criteria are met, and in a fourth set of earlier detected R-wave detections to thereby determine whether second TWO or PWO temporal criteria are met, wherein the fourth set differs from the third set but has some overlap with the third set; and classify the R-wave detection as a false R-wave detection also based on whether one of the first or the second TWO or PWO temporal criteria are met.

15. The IMD of claim 14, wherein:

the third set of earlier detected R-wave detections includes the R-wave detections that were one and two R-wave detections earlier;

the fourth set of earlier detected R-wave detections includes the R-wave detections that were two and three R-wave detections earlier;

the processor or controller is configured to determine that the first TWO or PWO temporal criteria are met when an R-R interval duration D (n) associated with the R-wave detection is dissimilar to an R-R interval duration D (n−1) associated with the R-wave detection that was one R-wave detection earlier, and is similar to an R-R interval duration D (n−2) associated with the R-wave detection that was two R-wave detections earlier; and the processor or controller is configured to determine that the second TWO or PWO temporal criteria are met when the R-R interval duration D (n) associated with the R-wave detection is dissimilar to the R-R interval duration D (n−2) associated with the R-wave detection that was two R-wave detections earlier, and is similar to an R-R interval duration D (n−3) associated with the R-wave detection that was three R-wave detections earlier.

16. The IMD of claim 15, wherein the processor or controller is configured to classify the R-wave detection as a false R-wave detection in response to:

both the first TWO or PWO morphological criteria and the first TWO or PWO temporal criteria being met; or both the second TWO or PWO morphological criteria and the second TWO or PWO temporal criteria being met.

17. The IMD of claim 9, wherein the processor or controller is configured to adjust the at least one parameter of the R-wave detection threshold in response to at least a threshold number of the R-wave detections within a specified number of the R-wave detections or within a specified amount of time being classified as false R-wave detections due to TWO or PWO.

18. A method for use by an implantable medical device (IMD), the method comprising:

sensing a signal indicative of electrical activity of a patient's heart;

detecting R-waves based on comparisons of the signal indicative of electrical activity of the patient's heart, or samples thereof, to an R-wave detection threshold;

detecting an arrhythmic episode based on the R-wave detections;

in response to the arrhythmic episode detection, for each R-wave detection of at least some of the R-wave detections in a window leading up to the arrhythmic episode detection, determining whether the R-wave detection should be classified as a false R-wave detection due to T-wave oversensing (TWO) or P-wave oversensing (PWO) by:

obtaining a peak amplitude A (n) associated with the R-wave detection and a respective peak amplitude for other R-wave detections preceding the R-wave detection;

determining whether first TWO or PWO morphological criteria are met by determining whether a peak amplitude A (n) associated with the R-wave detection is at least a specified extent lower than a peak amplitude A (n−1) associated with an R-wave detection that was one R-wave detection earlier, is not at least the specified extent lower than a peak amplitude A (n−2) associated with an R-wave detection that was two R-wave detections earlier, and is at least the specified extent lower than a peak amplitude A (n−3) associated with an R-wave detection that was three R-wave detections earlier;

determining whether second TWO or PWO morphological criteria are met by determining whether the peak amplitude A (n) associated with the R-wave detection is at least the specified extent lower than the peak amplitude A (n−2) associated with the R-wave detection that was two R-wave detections earlier, is not at least the specified extent lower than the peak amplitude A (n−3) associated with the R-wave detection that was three R-wave detections earlier, and is at least the specified extent lower than a peak amplitude A (n−4) associated with an R-wave detection that was four R-wave detections earlier; and classifying the R-wave detection as a false R-wave detection in response to one of the first or the second TWO or PWO morphological criteria being met; and based on an extent of the R-wave detections classified as being false R-wave detections due to TWO or PWO, performing at least one of: selectively preventing or aborting delivery of therapy by the IMD intended to treat the arrhythmic episode; selectively preventing transmission by the IMD to an external device of data corresponding to the arrhythmic episode that can be used for diagnostic purposes; or selectively adjusting at least one parameter of the R-wave detection threshold that can be used by the IMD for detecting further R-waves and thereby detecting a further arrhythmic episode.

19. An implantable medical device (IMD), comprising:
two or more electrodes;
a sensing circuitry coupled to at least two of the two or more electrodes and configured to obtain a signal indicative of electrical activity of a patient's heart; and
a processor or controller configured to detect an arrhythmic episode based on R-wave detections that are detected based on comparisons of the signal indicative of electrical activity of the patient's heart, or samples thereof, to an R-wave detection threshold;
wherein in response to the arrhythmic episode detection, for each R-wave detection of at least some of the R-wave detections in a window leading up to the arrhythmic episode detection, in order to determine whether the R-wave detection should be classified as a false R-wave detection due to T-wave oversensing (TWO) or P-wave oversensing (PWO), the processor or controller is configured to
obtain a peak amplitude A (n) associated with the R-wave detection and a respective peak amplitude for other R-wave detections preceding the R-wave detection;
determine whether first TWO or PWO morphological criteria are met by determining whether the peak amplitude A (n) associated with the R-wave detection is at least a specified extent lower than a peak amplitude A (n−1) associated with an R-wave detection that was one R-wave detection earlier, is not at least the specified extent lower than a peak amplitude A (n−2) associated with an R-wave detection that was two R-wave detections earlier, and is at least the specified extent lower than a peak amplitude A (n−3) associated with an R-wave detection that was three R-wave detections earlier;
determine whether second TWO or PWO morphological criteria are met by determining whether the peak amplitude A (n) associated with the R-wave detection is at least the specified extent lower than the peak amplitude A (n−2) associated with the R-wave detection that was two R-wave detections earlier, is not at least the specified extent lower than the peak amplitude A (n−3) associated with the R-wave detection that was three R-wave detections earlier, and is at least the specified extent lower than a peak amplitude A (n−4) associated with an R-wave detection that was four R-wave detections earlier; and
classify the R-wave detection as a false R-wave detection in response to one of the first or the second TWO or PWO morphological criteria being met; and
wherein based on an extent of the R-wave detections classified as being false R-wave detections due to TWO or PWO, the processor or controller is configured to at least one of: selectively prevent or abort delivery of therapy by the IMD intended to treat the arrhythmic episode; selectively prevent transmission by the IMD to an external device of data corresponding to the arrhythmic episode that can be used for diagnostic purposes; or selectively adjust at least one parameter of the R-wave detection threshold that can be used by the IMD to detect further R-waves and thereby detect a further arrhythmic episode.

\* \* \* \* \*